United States Patent
Zhu et al.

(10) Patent No.: US 9,481,636 B2
(45) Date of Patent: Nov. 1, 2016

(54) N-BENZYLANILINE DERIVATIVE AND USES THEREOF

(71) Applicant: Nanjing Medical University, Jiangsu (CN)

(72) Inventors: Dongya Zhu, Jiangsu (CN); Fei Li, Jiangsu (CN); Chunxia Luo, Jiangsu (CN)

(73) Assignee: NANJING MEDICAL UNIVERSITY, Jiangsu (CN)

(*) Notice: Subject to any disclaimer, the term of this patent is extended or adjusted under 35 U.S.C. 154(b) by 99 days.

(21) Appl. No.: 14/355,340

(22) PCT Filed: Oct. 24, 2012

(86) PCT No.: PCT/CN2012/083455
§ 371 (c)(1),
(2) Date: Apr. 30, 2014

(87) PCT Pub. No.: WO2013/064031
PCT Pub. Date: May 10, 2013

(65) Prior Publication Data
US 2014/0303248 A1    Oct. 9, 2014

(30) Foreign Application Priority Data

Nov. 3, 2011  (CN) .......................... 2011 1 0343293

(51) Int. Cl.
| | | |
|---|---|---|
| *C07C 229/00* | (2006.01) |
| *C07C 229/60* | (2006.01) |
| *A61K 31/196* | (2006.01) |
| *A61K 31/245* | (2006.01) |
| *C07C 233/54* | (2006.01) |
| *C07C 229/54* | (2006.01) |

(52) U.S. Cl.
CPC ........... *C07C 229/60* (2013.01); *A61K 31/196* (2013.01); *A61K 31/245* (2013.01); *C07C 229/54* (2013.01); *C07C 233/54* (2013.01); *C07C 2103/64* (2013.01)

(58) Field of Classification Search
CPC .............. A61K 31/196; A61K 31/245; C07C 2103/64; C07C 229/54; C07C 229/60; C07C 233/54
See application file for complete search history.

(56) References Cited

FOREIGN PATENT DOCUMENTS

| CN | 101492384 | * | 7/2009 |
| CN | 101792399 |   | 8/2010 |
| CN | 101817908 |   | 9/2010 |
| CN | 102516107 |   | 6/2012 |

OTHER PUBLICATIONS

STN 2009.*
Zhou et al. (Treatment of cerebral ischemia by disrupting ischemiainduced interaction of nNOS with PSD-95 Nature Medicince vol. 16, No. 12 published online Nov. 21, 2010).*
Arundine et al., "Molecular mechanisms of glutamate-dependant neurodegeneration in ischemia and traumatic brain injury," *Cell. Mol. Life Sci.*, 61: 657-668, (2004).
D'Mello et al., "Perturbing PSD-95 Interactions with NR2B-subtype Receptors Attenuates Spinal Nociceptive Plasticity and Neuropathic Pain," *Molecular Therapy*, 19(10): 1780-1792, (Oct. 2011).
Florio et al., "Disruption of nNOS-PSD95 protein-protein interaction inhibits acute thermal hyperalgesia and chronic mechanical allodynia in rodents," *British Journal of Pharmacology*, 158: 494-506, (2009).
Jones, "Disruption of the nNOS-PSD-95 complex is neuroprotective in models of cerebral ischemia," *Nature Reviews Neurology*, 7: 61, (Feb. 2011).
Lim et al., "Disruption of the NMDA receptor-PSD-95 interaction in hippocampal neurons with no obvious physiological short-term effect," *Neuropharmacology*, 45: 738-754, (2003).
Muir, "Glutamate-based therapeutic approaches: clinical trials with NMDA antagonists," *Current Opinion in Pharmacology*, 6: 53-60, (2006).
Ro et al., "The role of peripheral N-methyl-D-aspartate receptors in muscle hyperalgesia," *Neuroreport*, 16(5): 485-489, (Apr. 2005).
Sattler et al., "Specific Coupling of NMDA Receptor Activation to Nitric Oxide Neurotoxicity of PSD-95 Protein," *Science*, 284: 1845-1848, (Jun. 1999).
Soliman et al., "mGlu and NMDA receptor contributions to capsaicin-induced thermal and mechanical hypersensitivity," *Neuropharmacology*, 48: 325-332, (2005).

(Continued)

*Primary Examiner* — Yevegeny Valenrod
*Assistant Examiner* — Blaine G Doletski
(74) *Attorney, Agent, or Firm* — Knobbe Martens Olson & Bear LLP

(57) ABSTRACT

A N-benzylaniline derivative and uses thereof. The derivative is a compound represented by formula I or a pharmaceutically acceptable salt thereof. The compound protects against cerebral ischemia/reperfusion injury and has analgesic action for chronic pathologic pain, and may be used to treat cerebral apoplexy, neuropathic pain, and inflammatory pain. Moreover, because of the unique mechanism of action of the compound, the compound can be used to treat epilepsy, affective disorder, and neurodegenerative diseases.

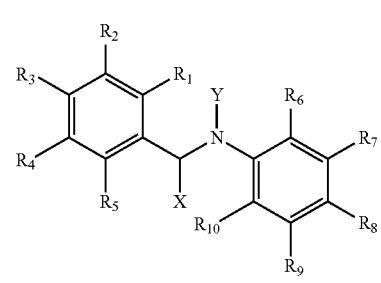

11 Claims, 8 Drawing Sheets

(56) References Cited

OTHER PUBLICATIONS

Woolf, "Evidence for a central component of post-injury pain hypersensitivity," *Nature*, 306: 686-688, (Dec. 1983).
Zhou et al., "Treatment of cerebral ischemia by disrupting ischemia-induced interaction of nNOS with PSD-95," *Nature Medicine*, 16(12): 1439-1443, (Dec. 2010).
International Search Report issued in International Application No. PCT/CN2012/083455 on Jan. 31, 2013.
Borbély et al., "Small-Molecule Inhibitors of NADPH Oxidase 4," Journal of Medicinal Chemistry, vol. 53, No. 18, pp. 6758-6762, 2010.
Chen et al., "Synthesis and Structure-Activity Studies of a Series of [(Hydroxybenzyl) Amino] Salicylates as Inhibitors of EGF Receptor-Associated Tyrosine Kinase Activity," Journal of Medicinal Chemistry, vol. 36, No. 25, pp. 4094-4098, 1993.
Smyth et al., "Non-Amine Based Analogues of Lavendustin A as Protein-Tyrosine Kinase Inhibitors," Journal of Medicinal Chemistry, vol. 36, No. 20, pp. 3010-3014, 1993.

\* cited by examiner

N-BENZYLANILINE DERIVATIVE AND USES THEREOF

This application is the U.S. National Phase under 35 U.S.C. §371 of International Application No. PCT/CN2012/083455, filed Oct. 24, 2012, designating the U.S., and published in Chinese as WO 2013/064031 on May 10, 2013, which claims priority to Chinese Patent Application No. 201110343293.X, filed Nov. 3, 2011, the entire content of which is incorporated herein by reference.

FIELD OF THE INVENTION

The present invention belongs to the field of pharmaceutical, and provides an N-benzylaniline derivative as well as preparation method and pharmaceutical use thereof.

BACKGROUND OF THE INVENTION

Stroke has characteristics of high mortality, high disability rate, high recurrence rate, etc. and is seriously harmful to human health. Due to the complexity of the fine structure of brain tissue, it is particularly sensitive and vulnerable to hypoxic-ischemic injuries. So far, therapeutic drugs with definite efficacy are rare in clinical practice. Studies have shown that the excessive release of excitatory amino acids such as glutamate under a condition of cerebral ischemia results in overstimulation of N-methyl-D-aspartate receptor (NMDAR), thereby nitric oxide (NO) is released pathologically through NMDAR-PSD-95-nNOS signaling pathway (*Science*, 1999, 284, 1845-1848; *Nature Medicine* 2010, 16, 1439-1443), in which nNOS is neuronal nitric oxide synthase and PSD-95 is postsynaptic density protein-95. NO with a strong oxidizing property itself will directly damage surface lipids and internal structures of the surrounding cells when NO is excessively released or cleared up insufficiently. On the other hand, great amount of oxygen anion free radicals ($O_2^-$·) produced during the cerebral ischemia-reperfusion react with NO to generate nitrite superoxide anion free radicals ($ONOO^-$·), which as a strong and stable oxidant will cause more severe damage to cells (*Cell. Mol. Life. Sci.*, 2004, 61, 657-668). Thus, NMDAR-mediated activation of nNOS is a key event to the excitotoxic occurrence of neurons. Although a number of drugs were developed based on the two target molecules, direct intervention with them often leads to severe side effects due to the very important physiological functions of NMDAR and nNOS (*Curr. Opin. Pharmacol.*, 2006, 6, 53-60). Selectively blocking the interaction of NMDAR with PSD-95 (*Science*, 2002, 298, 846-850) or nNOS with PSD-95 (*Nature Medicine* 2010, 16, 1439-1443) other than directly interfering NMDAR or nNOS may inhibit pathological release of NO after cerebral ischemia without affecting physiological functions of NMDAR and nNOS, raising the possibility of obtaining safe and effective therapeutic drugs against cerebral ischemia with no significant side effects. Moreover, the coupling of nNOS and PSD-95 is more ideal drug target as it is downstream in the whole signal pathway (*Neuropharmacology*, 2003, 45, 738-754).

The benzylaniline derivative 4-N-(2-hydroxy-3,5-dichlorobenzyl) aminosalicylic acid (ZL006), an nNOS-PSD-95 uncoupler, reduce NMDAR-mediated pathological NO release, display significant neuroprotective effect against glutamate-induced neuronal injury, and improve animal neurological deficits and reduce infarct volume caused by middle cerebral artery occlusion (MCAO) and reperfusion, without affecting the physiological functions of NMDAR and nNOS (*Nature Medicine* 2010, 16, 1439-1443). Moreover, ZL006 does not cause learning and memory impairment, behavioral abnormalities and other side effects that may be caused by directly interfering NMDAR or/and nNOS. Thus ZL006 is safer and is of great significance to the treatment of cerebral ischemic injury-related diseases (*Nature. Rev. Neurol.*, 2011, 7, 61).

Pain is an unpleasant feeling and emotional experience caused by tissue damage or potential tissue damage. Under normal physiological conditions, "pain is an alarm signal that warns the body is under threat", and is also a special protective function indispensable to the body. However, under pathological conditions, tissue damage (including neurogenic and inflammatory) can lead to hyperexcitability of spinal dorsal horn neurons, resulting in central sensitization and generally manifesting as hyperalgesia and allodynia clinically. Recent studies suggest that the balance between excitatory neurotransmitter receptor system and inhibitory neurotransmitter receptor system in the central nervous system (CNS) plays an important role in the maintenance of normal pain threshold.

A large number of experimental results have shown that glutamate is an important excitatory neurotransmitter in the process of nociceptive information transmission in the central nervous system, and it mainly acts on the ionotropic glutamate receptors including non-NMDA receptors and NMDA receptors, and metabotropic glutamate receptors. Wherein, NMDA receptors play a very important role in hyperalgesia process induced by peripheral tissue injury or nerve damage (*Nature*, 1983, 306, 686-688). Studies have shown that intrathecal injection of MK-801, a noncompetitive antagonist of NMDA receptor, can significantly alleviate mechanical allodynia and thermal hyperalgesia in capsaicin-induced mechanical and thermal hyperalgesia (*Neuropharmacology*, 2005, 48, 325~332). Intramuscular injection of AP-5, a competitive antagonist of NMDA receptor, can reduce complete Freund's adjuvant (CFA)-induced muscle hyperalgesia in a dose-dependent manner (*Neuroreport*, 2005, 16, 485~489). However, in view of the broad distribution and the extensive function of NMDA receptors in the central nervous system, the use of NMDA receptor antagonists will result in central toxic side effects in many aspects such as memory loss, insanity, and ataxia, which greatly limits the clinical application of NMDA receptor antagonists as analgesics. Therefore, it has become a new target for analgesic drug research by interfering the transmission of pain-related downstream signaling mediated by NMDA receptors, without affecting the function as a channel of the NMDA receptor itself. nNOS is an important signaling molecule in the NMDA receptor signaling pathway. nNOS can be selectively activated by NMDA receptor-mediated $Ca^{2+}$ influx. In addition to the direct binding to the NMDA receptor, PDZ-2 in PSD-95 interacts with the PDZ domain of nNOS, forming an NMDA receptor/PSD-95/nNOS ternary complex, which provides a platform for the selective activation of nNOS by NMDA receptors-mediated $Ca^{2+}$. Experiments have shown that interference with the coupling of PSD-95 and nNOS by small molecule compounds and polypeptides similar to the terminal of PSD-95 can significantly reduce the acute thermal hyperalgesia and chronic mechanical hyperalgesia in rodents (*Journal of Pain Research*, 2011, 158, 494-506). The pain models in rodents show that the nNOS-PSD-95 uncoupler, 2-[(1H-benzotriazole-5-amino)methyl]-4,6-dichlorophenol (IC87201), has significant inhibitory effects against mechanical hyperalgesia and thermal hyperalgesia, and may be developed as an analgesic drug with brand new mechanism of action (*Brit. J.*

Pharmacol., 2009, 158, 494-506). PSD-95 and nNOS uncoupling therefore provide a new approach for screening selective analgesic drugs.

The target of nNOS-PSD-95 uncoupler represented by ZL006 is in the central nervous system, and thus this type of drugs need a good distribution within the central nervous system. However, since this type of uncouplers have high hydrophilicity and are not adapted to oral absorption and distribution within the central nervous system, it is necessary to increase the lipophilicity of the molecules. The present inventors have found that new molecules formed by the esterification or amidation of hydrophilic groups in nNOS-PSD-95 uncoupler represented by ZL006 molecule, administered by the various routes of administration including parenteral administration, have good protective effects against cerebral ischemia and analgesic effects.

SUMMARY OF THE INVENTION

The Object of the Present Invention

The present invention provides a class of N-benzylaniline derivatives. The most prominent feature of this type of drugs is that they have a protective effect against cerebral ischemia-reperfusion injury and an analgesic effect against chronic pathological pain, and can be used to prepare a medicament for treating stroke, neuropathic pain and inflammatory pathological pain. Meanwhile, due to the unique mechanism of action of this type of drugs, they can also be used to prepare a medicament for treating epilepsy, diseases of affective disorder and various neurodegenerative diseases.

Technical Solution

A class of N-benzylaniline derivatives of formula

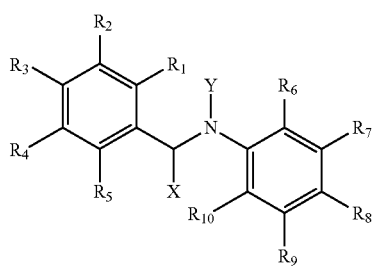

Formula I wherein, $R_1$ is hydroxyl, $C_1$-$C_6$ alkoxy or —$OCOR_{11}$, $R_2$, $R_3$, $R_4$, $R_5$, $R_6$, $R_9$ or $R_{10}$ is each independently hydrogen, halogen or trifluoromethyl;

$R_7$ or $R_8$ is each independently —$COR_{12}$, hydroxyl, $C_1$-$C_6$ alkoxy, —$OCH_2COR_{12}$, —$OCOR_{11}$ or —$OCH_2COB$;

X is hydrogen or $C_1$-$C_6$ alkyl;

Y is hydrogen, $C_1$-$C_6$ alkyl, —$CH_2COR_{13}$ or —$COR_{13}$;

$R_{11}$ is $C_1$-$C_6$ alkyl or B;

$R_{12}$ is $C_1$-$C_6$ alkyl, hydroxyl, $C_1$-$C_6$ alkoxy or B;

$R_{13}$ is $C_1$-$C_6$ alkyl, $C_1$-$C_6$ alkoxy or B;

B is

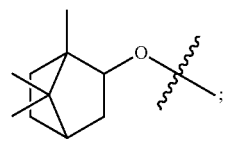 [SMILES: *OC1CC2CCC1(C)C2(C)C]

wherein when $R_2$, $R_4$ or $R_{10}$ is halogen, at least one of $R_7$, $R_8$ and Y contains B group, or X and Y are not both hydrogen;

or a pharmaceutically acceptable salt thereof.

In a preferred embodiment, at least one of $R_7$, $R_8$ and Y contains B group.

In another preferred embodiment, X and Y are not both hydrogen.

As a preference, $R_1$ is hydroxyl, $C_1$-$C_4$ alkoxy or $C_1$-$C_4$ alkoxycarbonyl, and further, $R_1$ is hydroxyl, methoxy or —$OCOCH_3$.

As a preference, $R_2$, $R_3$, $R_5$, $R_6$, $R_9$ or $R_{10}$ is each independently —H, —F, —Cl or —Br; $R_4$ is trifluoromethyl, —F, —Cl or —Br.

As a preference, $R_7$ is —COB, —OH, —$OCOR_{11}$, —$COR_{12}$, $C_1$-$C_6$ alkoxy or —$OCH_2COR_{12}$, and further, $R_7$ is —COB, —OH, —$OCOCH_3$, —$OCOC_3H_7$, —$OCOC_5H_{11}$, —$COOCH_3$, —COOH, —$COOC_2H_5$, —$OCH_3$, —$OC_4H_9$, —$OC_6H_{12}$, —$OCH_2COOCH_3$, —$OCH_2COOC_2H_5$ or —$OCH_2COB$.

As a preference, $R_8$ is —COB, —OH, —$OCOR_{11}$ or —$COR_{12}$, and further, $R_8$ is —COB, —OH, —$OCOCH_3$, —$COOCH_3$, —COOH or —$COOC_2H_5$.

As a preference, $R_{11}$ is $C_1$-$C_6$ linear alkoxy.

As a preference, $R_{12}$ is hydroxyl, $C_1$-$C_4$ linear alkoxy or B. Further, $R_{12}$ is hydroxyl, methoxy, ethoxy or —B.

As a preference, when $R_2$, $R_4$ or $R_{10}$ is halogen, $R_7$ or $R_8$ is —COB.

As a preference, X is hydrogen or $C_1$-$C_4$ alkyl; and further, X is hydrogen or methyl group.

As a preference, Y is hydrogen, $C_1$-$C_4$ linear alkyl, —$CH_2COR_{13}$, —$CH_2COB$ or —$COR_{13}$; and further, Y is hydrogen, —$CH_3$, —$COCH_3$, —$CH_2COOC_2H_5$, —$CH_2COB$ or —$CH_2COOCH_3$.

As a preference, $R_{13}$ is $C_1$-$C_4$ linear alkyl or $C_1$-$C_4$ linear alkoxy.

Unless otherwise stated, the following terms used in the specification and claims have the meanings as discussed below:

As mentioned in this application, the representing manner of the number of carbon atoms in a group, for example $C_1$-$C_{10}$, means that the group may contain 1 carbon atom, 2 carbon atoms, 3 carbon atoms, etc., and up to 10 carbon atoms.

An alkyl refers to a saturated aliphatic hydrocarbon including linear and branched hydrocarbon group, which includes, but are not limited to methyl, ethyl, propyl, isopropyl, n-butyl, isobutyl, tert-butyl, n-pentyl, n-hexyl and the like/

An alkoxy refers to an alkyl or cycloalkyl group linked through an oxygen linkage;

A halogen atom means fluorine, chlorine, bromine or iodine group;

The compounds provided by the present invention further comprise pharmaceutically acceptable equivalents of the compounds or a mixture of two or more thereof.

As a preference, the pharmaceutically acceptable equivalents of the compounds provided by the present invention may comprise one of pharmaceutically acceptable salt, hydrate, solvate, metabolite, prodrug or isostere, or a mixture of two or more thereof.

As a preference, among the pharmaceutically acceptable equivalents of the compounds provided by the present invention, the pharmaceutically acceptable salt comprises acid salt or basic salt of the compounds provided by the present invention. The pharmaceutically acceptable salt has the pharmaceutical activity of the compound and meets the requirements in biological and practical applications.

Among the pharmaceutically acceptable equivalents of the compounds provided by the present invention, the pharmaceutically acceptable acid salt includes, but are not limited to acetate, sulfate, phosphate, formate, propionate, adipate, succinate, tartrate, alginate, aspartate, benzoate, toluenesulfonate, methanesulfonate, benzenesulfonate, bisulfate, butyrate, citrate, camphorate, camphor sulfonate, cyclopentane propionate, digluconate, dodecylsulfate, ethanesulfonate, fumarate, glucoheptonate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, thiocyanate, tosylate and undecanoate.

As a preference, among the pharmaceutically acceptable equivalents of the compounds provided by the present invention, the pharmaceutically acceptable basic salt may include ammonium salt, alkali metal salt such as sodium and potassium salts, alkaline earth metal salt such as calcium and magnesium salts, and salt formed with organic base such as dicyclohexylamine salt, N-methyl-D glucamine salts, salt formed with amino acids such as arginine and lysine. Preferably, a group containing basic nitrogen may be quaternized by agents including, but not limiting to lower alkyl halides such as chloride, bromide and iodide of methyl, ethyl, propyl and butyl; dialkyl sulfates such as dimethyl, diethyl, dibutyl and diamyl sulfate; long chain halides such as chloride, bromide and iodide of decyl, lauryl, myristyl and stearyl; aralkyl halide such as phenyl bromides.

As a preference, among the pharmaceutically acceptable equivalents of the compounds provided by the present invention, a prodrug refers to a derivative of the compound of the present invention which requires biotransformation such as metabolism prior to showing its pharmacological effect. A prodrug is formulated with the substances that improve chemical stability, improve acceptance and compliance of a patient, improve bioavailability, prolong duration of action, improve organ selectivity, improve formulation such as increase water solubility, or reduce side effects such as toxicity. A prodrug can be prepared with the compound of the present invention by conventional methods, see BURGER'S MEDICINAL CHEMISTRY AND DRUG CHEMISTRY, 5th Edition, Vol. 1, pp. 172-178, 949-982 (1995).

In the present invention, an isostere refers to an element, a functional group, a substituent, a molecule or an ion with different molecular formula but exhibiting similar or the same physical properties. For example, tetrazole is an isostere of carboxylic acid, because it has similar properties to the carboxylic acid, even if they have different molecular formula. Typically, two isosteric molecules have similar or the same size and shape. Ideally, isosteric molecules are isomorphic and can be co-crystallized. Other physical properties of isostere molecules typically include boiling point, density, viscosity and thermal conductivity. However, since the outer orbital may be hybridized differently, certain properties such as dipolar moment, polarity, polarization, size and shape may be different. Isosteres include bioisosteres. In addition to the physical similarities, bioisosteres share certain biological properties. Typically, bioisosteres interact with the same recognition site thereof or broadly produce similar biological effects.

The compound of the present invention or pharmaceutically acceptable salt thereof can be formulated into various formulations that include, but are not limited to tablets, capsules, injections, lyophilized powder, etc.

Advantageous Effects

N-benzylaniline derivatives described in this patent are the substances that can dissociate the coupling of PSD-95-nNOS thereby avoids excessive NO production; this type of substances having protecting effects against cerebral ischemia/reperfusion injury and analgesic effects can be used to prepare a medicament for treating stroke, neuropathic pain and inflammatory pathological pain. Meanwhile, because of the unique mechanism of action of this type of drugs, they can also be used to prepare a medicament for treating epilepsy, diseases of affective disorder and various neurodegenerative diseases.

It is particularly emphasized that N-benzylaniline derivatives described in this patent can dissociate nNOS from PSD-95 and related proteins, thereby interfering with the NMDA receptor-PSD-95-nNOS pathway, without affecting the electric physiological activity of NMDA receptor and the catalytic activities of nNOS or other subtypes of NOS. As a result, the derivatives will not result in adverse reactions caused by blockage of NMDA receptor or inhibition of the enzymatic activity of nNOS, which has significant advantage for the treatment of chronic pathological pain, stroke and neurodegenerative diseases.

This patent provides a method for treating chronic pathological pain, narcotic tolerance, central nervous injury, neurodegenerative diseases, diseases of affective disorder by administering therapeutically effective amount of N-benzylaniline derivatives to a mammal (including a human) in need thereof. Specific diseases and conditions that can be treated include neuropathic pain, inflammatory pain, stroke, cerebral trauma, Parkinson's disease, epilepsy, Alzheimer's disease, amyotrophic lateral sclerosis and more other diseases.

Such N-benzylaniline derivatives may specifically uncouple nNOS-PSD-95 complex and exert treating effects for protecting against cerebral ischemic injury and relieving chronic pathological pain. In fact, the present invention provides a class of N-benzylaniline derivatives that are also used in the aspects for treating other neuropsychiatric disorders associated with interactions between nNOS and PSD-95 protein, such as central nervous system trauma, emotional disorders, epilepsy, neurodegenerative diseases including Parkinson's disease, Alzheimer's disease and Huntington's disease, and stroke, chronic pathological pain and so on.

DETAILED EMBODIMENTS

Figure 1:
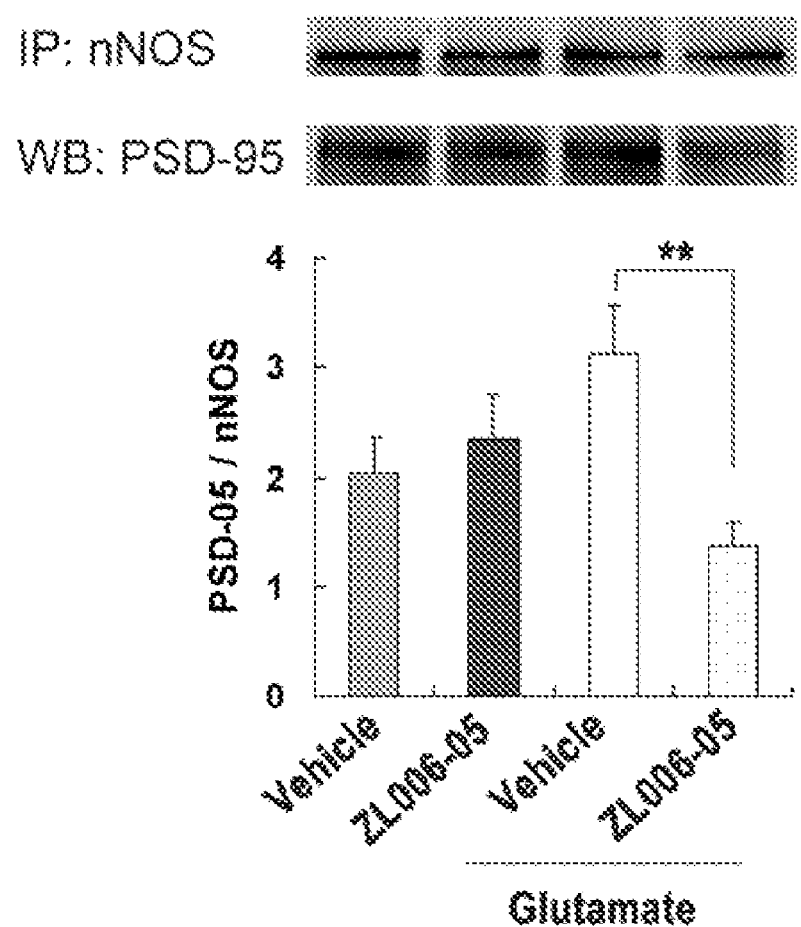
FIG. 1: ZL006-05 blocks glutamate-induced nNOS-PSD-95 coupling. Excitotoxicity was induced with glutamate in cultured primary neurons. ZL006-05 didn't affect the nNOS-PSD-95 coupling in normal cultured neurons, but significantly reduced the nNOS-PSD-95 coupling in injured neurons induced by glutamate. Mean±standard error, n=4, **$P<0.01$, compared with the vehicle group.

The following examples enable those skilled in the art to understand the present invention comprehensively, without limiting the invention in any way.

The structures of the compounds involved in the examples are shown in Table 1.

TABLE 1

Structures of the compounds involved in the examples

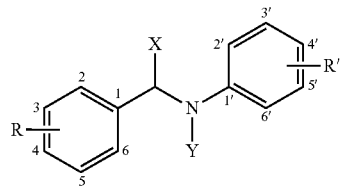

| | R | R' | X | Y |
|---|---|---|---|---|
| ZL006-01 | 2-OH, 3-Cl, 5-Cl | 3'-COB, 4'-OH | —H | —H |
| ZL006-02 | 2-OH, 3-Cl, 5-Cl | 3'-COB, 4'-OCOCH$_3$ | —H | —H |
| ZL006-03 | 2-OH, 5-Cl | 3'-COB, 4'-OH | —H | —H |
| ZL006-04 | 2-OH, 5-Br | 3'-COB, 4'-OH | —H | —H |
| ZL006-05 | 2-OH, 3-Cl, 5-Cl | 3'-OH, 4'-COB | —H | —H |
| ZL006-06 | 2-OH, 3-Cl, 5-Cl | 3'-OCOCH$_3$, 4'-COB | —H | —H |
| ZL006-07 | 2-OH, 3-Cl, 5-F | 3'-OCOCH$_3$, 4'-COB | —H | —H |
| ZL006-08 | 2-OH, 3-Cl, 5-F | 3'-OH, 4'-COB | —H | —H |
| ZL006-09 | 2-OH, 3-Cl, 5-Cl | 3'-OH, 4'-COOH | —H | —CH$_3$ |
| ZL006-10 | 2-OH, 3-Cl, 5-Cl | 3'-OCOCH$_3$, 4'-COOH | —H | —COCH$_3$ |
| ZL006-11 | 2-OH, 3-Cl, 5-F | 3'-COOCH$_3$, 4'-OH | —H | —CH$_3$ |
| ZL006-12 | 2-OH, 3-Cl, 5-Cl | 3'-COOH, 4'-OH | —H | —CH$_3$ |
| ZL006-13 | 2-OH, 3-Cl, 5-Cl | 3'-COOC$_2$H$_5$, 4'-COOC$_2$H$_5$ | —H | —CH$_3$ |
| ZL006-14 | 2-OH, 5-Cl | 3'-OH, 4'-COOH | —CH$_3$ | —H |
| ZL006-15 | 2-OH, 5-Br | 3'-OH, 4'-COOH | —CH$_3$ | —H |
| ZL006-16 | 2-OH, 3-Cl, 5-Cl | 2'-Cl, 4'-COB, 5'-OH | —H | —H |

TABLE 1-continued

Structures of the compounds involved in the examples

| | R | R' | X | Y |
|---|---|---|---|---|
| ZL006-17 | 2-OH, 3-Cl, 5-Cl | 2'-Cl, 3'-OH, 4'-COB | —H | —H |
| ZL006-18 | 2-OH, 3-Cl, 5-Cl | 2'-Cl, 4'-COB, 5'-OCOCH$_3$ | —H | —H |
| ZL006-19 | 2-OH, 3-Cl, 5-Cl | 2'-Cl, 3'-OCOCH$_3$, 4'-COB | —H | —H |
| ZL006-20 | 2-OH, 3-Cl, 5-Cl | 3'-OCH$_3$, 4'-COB | —H | —H |
| ZL006-21 | 2-OH, 3-Cl, 5-Cl | 3'-OC$_4$H$_9$, 4'-COB | —H | —H |
| ZL006-22 | 2-OH, 3-Cl, 5-Cl | 3'-OC$_6$H$_{12}$, 4'-COB | —H | —H |
| ZL006-23 | 2-OH, 3-Cl, 5-Cl | 3'-OCOC$_3$H$_7$, 4'-COB | —H | —H |
| ZL006-24 | 2-OH, 3-Cl, 5-Cl | 3'-OCOC$_5$H$_{11}$, 4'-COB | —H | —H |
| ZL006-25 | 2-OH, 3-Cl, 5-Cl | 2'-Cl, 4'-COB, 5'-OCH$_3$ | —H | —H |
| ZL006-26 | 2-OH, 3-Cl, 5-Cl | 2'-Cl, 3'-OCH$_3$, 4'-COB | —H | —H |
| ZL006-27 | 2-OH, 3-Cl, 5-Cl | 3'-OH, 4'-COB | —H | —CH$_3$ |
| ZL006-28 | 2-OH, 3-Cl, 5-Cl | 3'-OH, 4'-COB | —H | —COCH$_3$ |
| ZL006-29 | 2-OH, 3-Cl, 5-Cl | 3'-OCH$_3$, 4'-COB | —H | —CH$_3$ |
| ZL006-30 | 2-OH, 3-Cl, 5-Cl | 3'-OCOCH$_3$, 4'-COB | —H | —CH$_3$ |
| ZL006-31 | 2-OH, 3-Cl, 5-Cl | 3'-OCOC$_3$H$_7$, 4'-COB | —H | —COCH$_3$ |
| ZL006-32 | 2-OH, 3-Cl, 5-Cl | 3'-OCH$_2$COOCH$_3$, 4'-COB | —H | —H |
| ZL006-33 | 2-OH, 3-Cl, 5-Cl | 3'-OCH$_2$COB, 4'-COOCH$_3$ | —H | —H |
| ZL006-34 | 2-OH, 3-Cl, 5-Cl | 3'-OCH$_2$COOCH$_3$, 4'-COB | —H | —CH$_3$ |
| ZL006-35 | 2-OH, 3-Cl, 5-Cl | 3'-OCH$_2$COB, 4'-COOCH$_3$ | —H | —COCH$_3$ |
| ZL006-36 | 2-OH, 3-Cl, 5-Cl | 3'-OCH$_2$COOC$_2$H$_5$, 4'-COB | —H | —CH$_2$COOC$_2$H$_5$ |
| ZL006-37 | 2-OH, 3-Cl, 5-Cl | 3'-OCH$_2$COB, 4'-COB | —H | —CH$_2$COB |
| ZL006-38 | 2-OH, 3-Cl, 5-Cl | 3'-OCOCH$_3$, 4'-COOCH$_3$ | —H | —CH$_2$COB |
| ZL006-39 | 2-OH, 3-Cl,5-Br | 3'-OH, 4'-COB | —H | —H |
| ZL006-40 | 2-OH,3-Cl, 5-Br | 3'-COB, 4'-OH | —H | —H |
| ZL006-41 | 2-OH, 3-Cl, 5-Br | 3'-OCH$_3$, 4'-COB | —H | —H |
| ZL006-42 | 2-OH, 3-Cl, 5-Br | 3'-OC$_4$H$_9$, 4'-COB | —H | —H |
| ZL006-43 | 2-OH, 3-Cl, 5-Br | 3'-OCOCH$_3$, 4'-COB | —H | —H |
| ZL006-44 | 2-OH, 3-Cl, 5-Br | 3'-OCOC$_3$H$_7$, 4'-COB | —H | —H |
| ZL006-45 | 2-OH, 3-Cl, 5-Br | 3'-OH, 4'-COB | —H | —CH$_3$ |
| ZL006-46 | 2-OH, 3-Cl, 5-Br | 3'-OH, 4'-COB | —H | —COCH$_3$ |
| ZL006-47 | 2-OH, 3-Cl, 5-CF$_3$ | 3'-OH, 4'-COB | —H | —H |
| ZL006-48 | 2-OH, 3-Cl, 5-CF$_3$ | 3'-COB, 4'-OH | —H | —H |
| ZL006-49 | 2-OH, 3-Cl, 5-CF$_3$ | 3'-OCH$_3$, 4'-COB | —H | —H |
| ZL006-50 | 2-OH, 3-Cl, 5-CF$_3$ | 3'-OC$_4$H$_9$, 4'-COB | —H | —H |
| ZL006-51 | 2-OH, 3-Cl, 5-CF$_3$ | 3'-OCOCH$_3$, 4'-COB | —H | —H |
| ZL006-52 | 2-OH, 3-Cl, 5-CF$_3$ | 3'-OCOC$_3$H$_7$, 4'-COB | —H | —H |
| ZL006-53 | 2-OH, 3-Cl, 5-CF$_3$ | 3'-OH, 4'-COB | —H | —CH$_3$ |
| ZL006-54 | 2-OH, 3-Cl, 5-CF$_3$ | 3'-OH, 4'-COB | —H | —COCH$_3$ |
| ZL006-55 | 2-OH, 3-Cl, 5-F | 3'-OH, 4'-COB | —H | —H |
| ZL006-56 | 2-OH, 3-Cl, 5-F | 3'-COB, 4'-OH | —H | —H |
| ZL006-57 | 2-OH, 3-Cl, 5-F | 3'-OCH$_3$, 4'-COB | —H | —H |
| ZL006-58 | 2-OH, 3-Cl, 5-F | 3'-OC$_4$H$_9$, 4'-COB | —H | —H |
| ZL006-59 | 2-OH, 3-Cl, 5-F | 3'-OCOCH$_3$, 4'-COB | —H | —H |
| ZL006-60 | 2-OH, 3-Cl, 5-F | 3'-OCOC$_3$H$_7$, 4'-COB | —H | —H |
| ZL006-61 | 2-OH, 3-Cl, 5-F | 3'-OH, 4'-COB | —H | —CH$_3$ |
| ZL006-62 | 2-OH, 3-Cl, 5-F | 3'-OH, 4'-COB | —H | —COCH$_3$ |
| ZL006-63 | 2-OH, 5-Br | 3'-OH, 4'-COB | —H | —H |
| ZL006-64 | 2-OH, 5-Br | 3'-OCH$_3$, 4'-COB | —H | —H |
| ZL006-65 | 2-OH, 5-Br | 3'-OCOCH$_3$, 4'-COB | —H | —H |
| ZL006-66 | 2-OH, 5-Cl | 3'-OH, 4'-COB | —H | —H |
| ZL006-67 | 2-OH, 5-Cl | 3'-OCH$_3$, 4'-COB | —H | —H |
| ZL006-68 | 2-OH, 5-Cl | 3'-OCOCH$_3$, 4'-COB | —H | —H |
| ZL006-69 | 2-OH, 5-F | 3'-OH, 4'-COB | —H | —H |
| ZL006-70 | 2-OH, 5-F | 3'-OCH$_3$, 4'-COB | —H | —H |
| ZL006-71 | 2-OH, 5-F | 3'-OCOCH$_3$, 4'-COB | —H | —H |
| ZL006-72 | 2-OH, 5-CF$_3$ | 3'-OH, 4'-COB | —H | —H |
| ZL006-73 | 2-OH, 5-CF$_3$ | 3'-OCH$_3$, 4'-COB | —H | —H |
| ZL006-74 | 2-OH, 5-CF$_3$ | 3'-OCOCH$_3$, 4'-COB | —H | —H |
| ZL006-75 | 2-OCH$_3$, 3-Cl, 5-Cl | 3'-OH, 4'-COB | —H | —H |
| ZL006-76 | 2-OCOCH$_3$, 3-Cl, 5-Cl | 3'-OH, 4'-COB | —H | —H |
| ZL006-77 | 2-OCH$_3$, 3-Cl, 5-Br | 3'-OH, 4'-COB | —H | —H |
| ZL006-78 | 2-OCOCH$_3$, 3-Cl, 5-Br | 3'-OH, 4'-COB | —H | —H |
| ZL006-79 | 2-OCH$_3$, 3-Cl, 5-CF$_3$ | 3'-OH, 4'-COB | —H | —H |
| ZL006-80 | 2-OCOCH$_3$, 3-Cl, 5-CF$_3$ | 3'-OH, 4'-COB | —H | —H |

TABLE 1-continued

Structures of the compounds involved in the examples

| | R | R' | X | Y |
|---|---|---|---|---|
| ZL006-81 | 2-OH, 3-Cl, 5-Cl | 3'-OCOCH₃, 4'-COOCH₃ | —H | —COCH₃ |
| ZL006-82 | 2-OH, 3-Cl, 5-Br | 3'-OCOCH₃, 4'-COOCH₃ | —H | —COCH₃ |
| ZL006-83 | 2-OH, 3-Cl, 5-CF₃ | 3'-OCOCH₃, 4'-COOCH₃ | —H | —COCH₃ |

B =

Syntheses of the compounds involved in the examples:

Synthetic routes of the objective compounds (IV, V) are as follows:

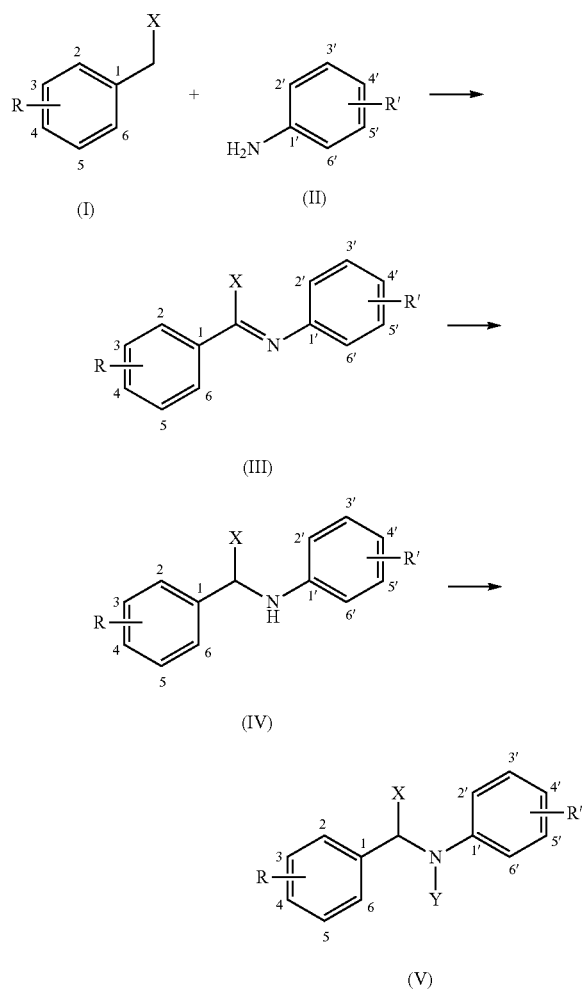

The objective compound (IV) was obtained by reducing the imine (III), which was obtained by reacting the substituted aldehyde or ketone (I) with specific aniline derivative (II), and the compound (V) was obtained by alkylating or acylating of the amino of the objective compound (IV).

The following examples describe the synthetic methods of the compounds in detail, which enables those skilled in the art to understand the present invention comprehensively without limiting the invention in any way.

Example 1 bornyl-2-hydroxy-5-(2-hydroxy-3,5-dichlorobenzyl) aminobenzoate (ZL006-01)

5-Nitrosalicyloyl chloride: 5-nitrosalicylic acid 3.66 g (0.02 mol), thionyl chloride 35 mL were added into a 100 mL eggplant-shaped flask. The reaction was stirred at room temperature for 2 h under a drying tube of anhydrous calcium chloride and then refluxed for 10 h. The reaction was stopped, distilled under reduced pressure to remove unreacted thionyl chloride, and cooled to give a yellowish-brown solid (3.82 g, yield 95.0%).

bornyl-5-nitrosalicylate: pyridine 10 ml, 2-borneol 3.08 g (0.02 mol) were added into a 50 mL eggplant-shaped flask and stirred until 2-borneol was completely dissolved. A solution of 5-nitrosalicyloyl chloride (3.80 g) in acetone (10 ml) was added dropwise under ice-water bath, after which the bottleneck was sealed with a drying tube of anhydrous calcium chloride, and the reaction was continued for 12 h. Acetone was removed by rotary evaporation, then 20 mL of ethyl acetate was added to the eggplant-shaped flask, and the reaction mass was transferred to a 100 mL separatory funnel. Pyridine was removed with 3% wt HCl solution (50 mL×3), and then the residue was purified by a silica gel column with the eluent of petroleum ether: ethyl acetate (v/v)=50:1 to give a white solid (1.59 g, yield 26.3%).

¹HNMR (300 MHz, DMSO-d6) δ: 0.88-2.32 (m, 16H), 5.05-5.08 (m, 1H), 7.71-7.72 (d, 1H), 7.74 (s, 1H), 7.94-7.97 (dd, 1H), 11.05 (s, 1H)

ethanol 150 mL, Raney nickel 1 g and bornyl-5-nitrosalicylate 1.59 g were added into a 500 mL high pressure reactor. After purged with hydrogen gas for 3 times, the reaction was carried out under 10 kg hydrogen gas pressure at 30° C. for 12 h. The reaction solution was distilled under reduced pressure and concentrated to about 50 mL, then transferred to a 100 mL eggplant-shaped flask, to which was added 3,5-dichlorosalicylaldehyde 0.80 g. The reaction solution was warmed to reflux temperature and refluxed for 1 h, then was allowed to stand under 0° C. to give a precipitated red solid, filtered to afford a red solid (1.38 g, yield 60.0%). To a 100 mL eggplant-shaped flask was added 10 mL ethanol, 0.2 g sodium borohydride and the prepared red solid, and the reaction was stirred for 2 h to give a clarified solution. 40 mL water was added dropwise with stirring for half an hour to precipitate a white material, which was filtered to afford an off-white powder (1.20 g, yield 86.4%).

$^1$HNMR (500 MHz, DMSO-d6) δ: 0.71-2.30 (m, 16H), 4.21 (s, 2H), 4.69-4.91 (m, 1H), 6.12 (s, 1H), 6.67-6.68 (d, 1H), 6.80-6.82 (dd, 1H), 6.92-6.94 (d, 1H), 6.97-6.99 (d, 1H), 7.35-7.36 (d, 1H). MS (M+H)$^+$: 464.1.

Example 2 bornyl-2-acetyloxy-5-(2-hydroxy-3,5-dichlorobenzyl) aminobenzoate (ZL006-02)

The synthesis of 2-acetyloxy-5-nitrobenzoic acid: to a 50 mL eggplant-shaped flask was added 5-nitrosalicylic acid 3.66 g (0.02 mol), acetic anhydride 4 mL (about 0.04 mol), stirred for 10 min, then continued with stirring for 30 min after addition of 2 drops of concentrated sulfuric acid. The reaction was stopped and the reaction mass was poured into 100 mL beaker. 60 mL water was added and stirred for 10 min to give a precipitated off-white material, which was filtered and the filter cake was washed with water for 3 times (50 mL×3), dried to give an off-white solid (4.14 g, yield 92.0%).

With the method of Example 1, the title compound was synthesized with starting materials of 2-acetyloxy-5-nitrobenzoic acid, 2-borneol and 3,5-dichlorosalicylaldehyde, as an off-white powder (yield 21.4% calculated based on 2-acetyloxy-5-nitrobenzoic acid).

$^1$HNMR (300 MHz, DMSO-d6) δ: 0.77-1.81 (m, 16H), 2.18 (s, 3H), 4.24 (s, 2H), 4.62-4.64 (d, 1H), 6.57 (s, 1H), 6.85-6.87 (d, 2H), 6.91-6.94 (d, 1H), 7.07-7.08 (d, 1H), 7.35-7.38 (dd, 1H). MS (M+H)$^+$: 506.1.

Example 3 bornyl-2-hydroxy-5-(2-hydroxy-5-chlorobenzyl) aminobenzoate (ZL006-03)

With the method of Example 1, the title compound was synthesized with starting materials of 2-hydroxy-5-nitrobenzoic acid, 2-borneol and 5-chlorosalicylaldehyde, as an off-white powder (yield 18.4% calculated based on 5-nitrosalicylic acid).

$^1$HNMR (300 MHz, DMSO-d6) δ: 0.73-1.82 (m, 16H), 2.18 (s, 3H), 4.17 (s, 2H), 4.65-4.67 (d, 1H), 6.47 (s, 1H), 6.82-6.84 (d, 2H), 6.89-6.91 (d, 1H), 6.94-6.95 (d, 1H), 7.08-7.10 (d, 2H). MS (M+H)$^+$: 430.2.

Example 4 bornyl-2-hydroxy-5-(2-hydroxy-5-bromobenzyl) aminobenzoate (ZL006-04)

With the method of Example 1, the title compound was synthesized with starting materials of 2-hydroxy-5-nitrobenzoic acid, 2-borneol and 5-bromosalicylaldehyde, as an off-white powder (yield 22.6%, calculated based on 2-hydroxy-5-nitrobenzoic acid).

$^1$HNMR (300 MHz, DMSO-d6) δ: 0.74-1.83 (m, 16H), 2.17 (s, 3H), 4.16 (s, 2H), 4.65-4.73 (m, 1H), 6.44 (s, 1H), 6.78-6.80 (d, 1H), 6.81-6.83 (dd, 1H), 6.89-6.91 (d, 1H), 6.94-6.95 (d, 1H), 7.19-7.21 (dd, 1H), 7.22 (s, 1H). MS (M+H)$^+$: 474.10.

Example 5 bornyl-2-hydroxy-4-(2-hydroxy-3,5-dichlorobenzyl) aminobenzoate (ZL006-05)

With the method of Example 1, the title compound was synthesized with starting materials of 4-nitrosalicylic acid, 2-borneol and 3,5-dichlorosalicylaldehyde, as an off-white powder (yield 24.6%, calculated based on 4-nitrosalicylic acid).

$^1$HNMR (300 MHz, DMSO-d6) δ: 0.85-2.05 (m, 16H), 4.31 (s, 2H), 4.97-4.99 (d, 1H), 5.94-5.95 (d, 1H), 6.23-6.25 (dd, 1H), 7.09-7.10 (d, 1H), 7.14 (s, 1H), 7.38-7.39 (d, 1H), 7.53-7.55 (d, 1H). $^{13}$CNMR (30 MHz, DMSO-d6) δ: 13.398, 18.594, 19.460, 26.859, 27.563, 36.337, 40.890, 44.278, 47.409, 48.621, 79.314, 96.780, 100.506, 105.761, 121.766, 123.328, 126.216, 127.241, 130.179, 130.699, 149.500, 154.646, 162.950, 169.7340. MS (M+H)$^+$: 464.1.

Example 6 bornyl-2-acetyloxy-4-(2-hydroxy-3,5-dichlorobenzyl) aminobenzoate (ZL006-06)

With the method of Example 1, the title compound was synthesized with starting materials of 2-acetyloxy-4-nitrobenzoic acid, 2-borneol and 3,5-dichlorosalicylaldehyde, as an off-white powder (yield 21.6%, calculated based on 2-acetyloxy-4-nitrobenzoic acid).

$^1$HNMR (500 MHZ, DMSO-d6) δ: 0.85-2.37 (m, 16H), 2.18 (s, 3H), 4.30 (s, 2H), 4.97 (s, 1H), 5.95 (s, 1H), 6.24-6.25 (dd, 1H), 7.10-7.11 (d, 1H), 7.14 (s, 1H), 7.39-7.40 (d, 1H), 7.54-7.56 (d, 1H), 9.76 (s, 1H). MS (M+H)$^+$: 506.1.

Example 7 bornyl-2-acetyloxy-4-(2-hydroxy-3-chloro-5-fluorobenzyl) aminobenzoate (ZL006-07)

With the method of Example 1, the title compound was synthesized with starting materials of 2-acetyloxy-4-nitrobenzoic acid, 2-borneol and 3-chloro-5-fluorosalicylaldehyde, as an off-white powder (yield 20.4%, calculated based on 2-acetyloxy-4-nitrobenzoic acid).

$^1$HNMR (300 MHZ, DMSO-d6) δ: 0.74-1.99 (m, 16H), 2.28 (s, 3H), 4.21 (s, 2H), 4.89-4.92 (d, 1H), 6.49 (s, 1H), 6.77-6.78 (d, 1H), 6.79-6.82 (d, 1H), 6.83-6.87 (dd, 1H), 6.89-6.93 (dd, 1H), 6.95 (d, 1H), 7.07-7.08 (d, 1H), 9.54 (s, 1H) MS (M+H)$^+$: 490.2.

Example 8 bornyl-2-hydroxy-4-(2-hydroxy-3-chloro-5-fluorobenzyl) aminobenzoate (ZL006-08)

With the method of Example 1, the title compound was synthesized with starting materials of 4-nitrosalicylic acid, 2-borneol and 3-chloro-5-fluorosalicylaldehyde, as an off-white powder (yield 20.8%, calculated based on 4-nitrosalicylic acid).

¹HNMR (300 MHz, DMSO-d6) δ: 0.74-1.92 (m, 16H), 4.13 (s, 2H), 4.94-4.97 (d, 1H), 5.96-5.98 (d, 1H), 6.78 (s, 1H), 6.80-6.81 (d, 1H), 6.88-6.89 (d, 1H), 6.91 (s, 2H), 6.94-6.95 (d, 1H). MS (M+H)$^+$: 448.2.

Example 9

2-hydroxy-4-[N-(2-hydroxy-3,5-dichlorobenzyl)-N-methyl]aminobenzoic acid (ZL006-09)

2-Hydroxy-4-(2-hydroxy-3,5-dichlorobenzylamino)benzoic acid (ZL006) 1.64 g (0.005 mol) was dissolved in 50 mL ethanol and 37% aqueous formaldehyde 6 mL (0.080 mmol) was added. The reaction was refluxed for 10 min, allowed to stand and cooled until a large amount of white solid precipitated, filtered and the filter cake was washed with ethanol to give an imine. The white solid was dispersed in 30 mL anhydrous ethanol, stirred for 30 min after the addition of NaBH$_4$ 1.5 g (0.080 mmol). After completion by TLC (petroleum ether:ethyl acetate (v/v)=5:1), the reaction was adjusted to pH 6~7 with concentrated hydrochloric, filtered and the filter cake was washed with anhydrous ethanol. The filtrates were combined and purified by silica gel column chromatography with a mobile phase of petroleum ether:ethyl acetate (v/v)=15:1. The eluates were collected and combined, concentrated to a total volume of about 15 mL, filtered and dried under vacuum to give an off-white powder (1.04 g, yield 61.3%).

¹HNMR (300 MHz, DMSO-d6) δ: 3.10 (s, 3H), 4.58 (s, 2H), 6.04-6.05 (d, 1H), 6.23-6.35 (dd, 1H), 6.75-6.76 (d, 1H), 7.40-7.41 (d, 1H), 7.53-7.55 (d, 1H), 9.81 (s, 1H), 11.40 (s, 1H). 12.98 (s, 1H). MS (M+H)$^+$: 342.0.

Example 10

2-acetyloxy-4-[N-(2-hydroxy-3,5-dichlorobenzyl)-N-acetyl]aminobenzoic acid (ZL006-10)

To a 50 mL eggplant-shaped flask was added 2-hydroxy-4-(2-hydroxy-3,5-dichlorobenzylamino)benzoic acid (ZL006) 3.28 g (0.01 mol), and acetic anhydride 6 mL (about 0.06 mol) dropwise with stirring. The reaction was then stirred for 5 min, and continued with stirring for 30 min after 3~4 drops of concentrated sulfuric acid were added dropwise. The reaction was stopped and the reaction mass was poured into 100 mL beaker. 60 mL water was added and stirred for 10 min to give a precipitated grey material, which was filtered and the filter cake was washed with water 3 times (50 mL×3), dried to give a grey solid (3.67 g, yield 89.0%).

¹HNMR (300 MHz, DMSO-d6) δ: 2.24 (s, 3H), 2.26 (s, 3H), 4.88 (s, 2H), 7.21-7.22 (d, 1H), 7.25 (s, 1H), 7.26-7.27 (d, 1H), 7.66-7.67 (d, 1H), 7.90-7.91 (d, 1H). MS (M+H)$^+$: 412.0.

Example 11 methyl 2-hydroxy-5-[N-(2-hydroxy-3-chloro-5-fluorobenzyl)-N-methyl]aminobenzoate (ZL006-11)

With the method of Example 9, the title compound was synthesized with starting materials of methyl 2-hydroxy-4-(2-hydroxy-3-chloro-5-fluorobenzylamino)benzoate, as an off-white powder (yield 59.8%, calculated based on methyl 2-hydroxy-4-(2-hydroxy-3-chloro-5-fluorobenzylamino)benzoate).

¹HNMR (500 MHz, DMSO-d6) δ: 1.26-1.30 (t, 3H), 3.11 (s, 3H), 4.25-4.26 (d, 2H), 6.64-6.67 (m, 2H), 6.92-6.94 (dd, 1H), 7.23-7.25 (dd, 1H), 7.47-7.49 (d, 1H).

MS (M+H)$^+$: 340.1.

Example 12

2-hydroxy-5-[N-(2-hydroxy-3,5-dichlorobenzyl)-N-methyl]aminobenzoic acid (ZL006-12)

With the method of Example 9, the title compound was synthesized with starting materials of 2-hydroxy-4-(2-hydroxy-3,5-dichloro-benzylamino)benzoic acid, as an off-white powder (yield 62.1%, calculated based on methyl 2-hydroxy-4-(2-hydroxy-3,5-dichloro-benzylamino)benzoate).

¹HNMR (500 MHz, DMSO-d6) δ: 1.26-1.30 (t, 3H), 3.11 (s, 3H), 4.26 (q, 2H), 4.30 (d, 2H), 5.94-5.95 (d, 1H), 6.21-6.23 (dd, 1H), 7.11-7.16 (m, 2H), 7.39-7.40 (d, 1H), 7.48-7.51 (d, 1H). MS (M+H)$^+$: 342.0

Example 13 diethyl 4-[N-(3,5-dichloro-2-hydroxybenzyl)-N-methyl]aminophthalate (ZL006-13)

With the method of Example 9, the title compound was synthesized with starting materials of diethyl 4-(2-hydroxy-3,5-dichlorobenzylamino)-phthalate, as an off-white powder (yield 62.4%, calculated based on diethyl 4-(2-hydroxy-3,5-dichlorobenzylamino)-phthalate).

¹HNMR (500 MHz, DMSO-d6) δ: 3.71 (s, 3H), 3.76 (s, 3H), 4.34 (d, 2H), 6.65-6.68 (m, 2H), 7.16-7.13 (m, 2H), 7.61-7.62 (d, 1H). MS (M+H)$^+$: 426.1

Example 14

2-hydroxy-4-[1-(2-hydroxy-5-chlorophenyl)]-ethyl-aminobenzoic acid (ZL006-14)

To a 50 mL single-neck flask was added 5-chloro-o-hydroxyacetophenone 0.8 g (0.005 mol), p-aminosalicylic acid 4.0 g (0.026 mol), anhydrous ethanol 20 ml, and glacial acetic acid was added dropwise to the solution until pH=6. The reaction mixture was refluxed for 24 h in oil bath, cooled and allowed to stand. Water was added dropwise to the reaction mixture, no solid precipitated. The reaction mixture was filtered to give a yellow solid of approximately 0.8 g. To a 50 mL single-neck flask was added the yellow solid and 10 mL anhydrous ethanol. The mixture was stirred at room temperature, then NaBH$_4$ was slowly added. The reaction was completed when the yellow solution converted to colourless. The mixture was added concentrated hydrochloric acid dropwise to pH=7, and the precipitated solid was filtered to give the title compound 0.19 g, as an off-white powder (yield 12.2%, calculated based on 5-chloro-o-hydroxyacetophenone).

¹HNMR (500 MHz, DMSO-d6) δ: 1.26-1.27 (d, 3H), 4.10-4.12 (m, 1H), 5.97 (s, 1H), 6.07 (s, 1H), 6.75-6.77 (t, 1H), 7.20-7.21 (d, 1H), 7.29-7.30 (d, 1H). MS (M+H)$^+$: 308.1

Example 15

2-hydroxy-4-[1-(2-hydroxy-5-bromo-phenyl)]ethyl-aminobenzoic acid (ZL006-15)

With the method of Example 14, the title compound was synthesized with starting materials of 5-bromo-o-hydroxyacetophenone, p-aminosalicylic acid, as an off-white powder (yield 11.6%, calculated based on 5-bromo-o-hydroxyacetophenone).

$^1$HNMR (500 MHz, DMSO-d6) δ: 1.31 (d, 3H), 4.62 (m, 1H), 5.94 (m, 4H), 6.77 (m, 2H), 7.15 (dd, 1H), 7.30 (d, 1H) MS (MαH)$^+$: 352.0

Example 16 bornyl-2-hydroxy-4-(2-hydroxy-3,5-dichlorobenzyl) amino-5-chlorobenzoate (ZL006-016)

With the method of Example 1, bornyl-4-aminosalicylate was synthesized with starting materials of 4-nitrosalicylic acid and 2-borneol.

To a 50 mL eggplant-shaped flask was added glacial acetic acid 20 ml, bornyl-4-aminosalicylate 2.89 g (0.01 mol), and stirred to complete dissolution. Chlorine gas was bubbled into the mixture in an ice-water bath until the total weight of the eggplant-shaped flask and its contents increased by 0.75 g (0.0105 mol). The reaction was stirred at room temperature for 12 h. The mixture was poured into 100 g of ice water, filtered and purified by silica gel column with an eluant (petroleum ether:ethyl acetate (v/v)=50:1) to give a white solid of 2-borneol 3-chloro-4-aminosalicylate (0.65 g, yield 20.1%). 2-Borneol 4-amino-5-chlorosalicylate (0.77 g, yield 24.1%).

bornyl-3-chloro-4-amino salicylate $^1$HNMR (300 MHz, DMSO-d6) δ: 0.85-2.05 (m, 16H), 4.98-5.00 (d, 1H), 6.34-6.37 (d, 1H), 7.45-7.47 (d, 1H).

bornyl-4-amino-5-chlorosalicylate $^1$HNMR (300 MHz, DMSO-d6) δ: 0.85-2.05 (m, 16H), 4.98-5.00 (s, 1H), 6.26 (s, 1H), 7.56 (s, 1H).

With the method of Example 1, bornyl-2-hydroxy-4-(2-hydroxy-3,5-dichlorobenzyl)amino-5-chlorobenzoate (ZL006-16) was synthesized with starting materials of bornyl-4-amino-5-chlorosalicylate, 3,5-dichlorosalicylaldehyde, as a light green powder (yield 72.2%, calculated based on bornyl-4-amino-5-chlorosalicylate).

$^1$HNMR (300 MHz, DMSO-d6) δ: 0.85-2.05 (m, 16H), 4.31 (s, 2H), 4.97-4.99 (d, 1H), 5.94-5.95 (d, 1H), 6.26 (s, 1H), 7.09-7.10 (d, 1H), 7.14 (s, 1H), 7.38-7.39 (d, 1H), 7.56 (s, 1H). MS (M+H)$^+$: 498.1

Example 17 bornyl-2-hydroxy-3-chloro-4-(2-hydroxy-3,5-dichlorobenzyl)aminobenzoate (ZL006-017)

With the method of Example 1, the title compound was synthesized with starting materials of bornyl-3-chloro-4-aminosalicylate (see Example 16 for the preparation method), 3,5-dichlorosalicylaldehyde, as a light green powder (yield 70.4%, calculated based on bornyl-4-amino-5-chlorosalicylate).

$^1$HNMR (300 MHz, DMSO-d6) δ: 0.85-2.05 (m, 16H), 4.31 (s, 2H), 4.97-4.99 (d, 1H), 5.94-5.95 (d, 1H), 6.34-6.37 (d, 1H), 7.09-7.10 (d, 1H), 7.14 (s, 1H), 7.38-7.39 (d, 1H), 7.45-7.47 (d, 1H). MS (M+H)$^+$: 498.1

Example 18 bornyl-2-acetyloxy-4-(2-hydroxy-3,5-dichlorobenzyl) amino-5-chlorobenzoate (ZL006-018)

With the method of Example 1, the title compound was synthesized with starting materials of 2-bornyl 2-acetyloxy-4-amino-5-chlorobenzoate and 3,5-dichlorosalicylaldehyde, as an off-white powder (yield 71.6%, calculated based on 2-bornyl 2-acetyloxy-4-amino-5-chlorobenzoate).

$^1$HNMR (300 MHz, DMSO-d6) δ: 0.85-2.37 (m, 16H), 2.18 (s, 3H), 4.30 (s, 2H), 4.97 (s, 1H), 5.94-5.95 (d, 1H), 6.26 (s, 1H), 7.09-7.10 (d, 1H), 7.14 (s, 1H), 7.38-7.39 (d, 1H), 7.56 (s, 1H). MS (M+H)$^+$: 540.1

Example 19 bornyl-2-acetyloxy-3-chloro-4-(2-hydroxy-3,5-dichlorobenzyl)aminobenzoate (ZL006-019)

With the method of Example 1, the title compound was synthesized with starting materials of 2-bornyl 2-acetyloxy-3-chloro-4-aminobenzoate and 3,5-dichlorosalicylaldehyde, as an off-white powder (yield 72.5%, calculated based on 2-bornyl 2-acetyloxy-3-chloro-4-aminobenzoate).

$^1$HNMR (300 MHz, DMSO-d6), δ: 0.85-2.37 (m, 16H), 2.18 (s, 3H), 4.30 (s, 2H), 4.97 (s, 1H), 5.94-5.95 (d, 1H), 6.34-6.37 (d, 1H), 7.09-7.10 (d, 1H), 7.14 (s, 1H), 7.38-7.39 (d, 1H), 7.45-7.47 (d, 1H). MS (M+H)$^+$: 540.1

Example 20 bornyl-2-methoxy-4-(2-hydroxy-3,5-dichlorobenzyl) aminobenzoate (ZL006-020)

With the method of Example 1, the title compound was synthesized with starting materials of 4-nitrosalicylic acid, 2-borneol and 2-methoxy-3,5-dichlorobenzaldehyde, as an off-white powder (yield 62.8%, calculated based on 4-nitrosalicylic acid).

$^1$HNMR (300 MHz, DMSO-d6) δ: 0.85-2.05 (m, 16H), 3.83 (s, 3H), 4.31 (s, 2H), 4.97-4.99 (d, 1H), 5.94-5.95 (d, 1H), 6.23-6.25 (dd, 1H), 7.09-7.10 (d, 1H), 7.14 (s, 1H), 7.38-7.39 (d, 1H), 7.53-7.55 (d, 1H). MS (M+H)$^+$: 478.2

Example 21 bornyl-2-n-butoxy-4-(2-hydroxy-3,5-dichlorobenzyl) aminobenzoate (ZL006-021)

With the method of Example 1, the title compound was synthesized with starting materials of 4-nitrosalicylic acid, 2-borneol and 2-n-butoxy-3,5-dichlorobenzaldehyde, as an off-white powder (yield 62.2%, calculated based on 4-nitrosalicylic acid).

$^1$HNMR (300 MHz, DMSO-d6) δ: 0.85-2.05 (m, 23H), 4.05-4.07 (1, 2H), 4.31 (s, 2H), 4.97-4.99 (d, 1H), 5.94-5.95

Example 22 bornyl-2-n-hexyloxy-4-(2-hydroxy-3,5-dichlorobenzyl) aminobenzoate (ZL006-022)

With the method of Example 1, the title compound was synthesized with starting materials of 4-nitrosalicylic acid, 2-borneol and 2-n-hexyloxy-3,5-dichlorobenzaldehyde, as an off-white powder (yield 63.1%, calculated based on 4-nitrosalicylic acid).
$^1$HNMR (300 MHz, DMSO-d6) δ: 0.85-2.05 (m, 27H), 4.05-4.07 (1, 2H), 4.31 (s, 2H), 4.97-4.99 (d, 1H), 5.94-5.95 (d, 1H), 6.23-6.25 (dd, 1H), 7.09-7.10 (d, 1H), 7.14 (s, 1H), 7.38-7.39 (d, 1H), 7.53-7.55 (d, 1H). MS (M+H)$^+$: 548.2

Example 23 bornyl-2-butyryloxy-4-(2-hydroxy-3,5-dichlorobenzyl) aminobenzoate (ZL006-023)

With the method of Example 1, the title compound was synthesized with starting materials of 2-butyryloxy-4-nitrobenzoic acid, 2-borneol and 3,5-dichlorosalicylaldehyde, as an off-white powder (yield 63.1%, calculated based on 2-butyryloxy-4-nitrobenzoic acid).
$^1$HNMR (500 MHZ, DMSO-d6) δ: 0.85-2.37 (m, 23H), 4.30 (s, 2H), 4.97 (s, 1H), 5.95 (s, 1H), 6.24-6.25 (dd, 1H), 7.10-7.11 (d, 1H), 7.14 (s, 1H), 7.39-7.40 (d, 1H), 7.54-7.56 (d, 1H). MS (M+H)$^+$: 534.2

Example 24 bornyl-2-hexanoyloxy-4-(2-hydroxy-3,5-dichlorobenzyl) aminobenzoate (ZL006-024)

With the method of Example 1, the title compound was synthesized with starting materials of 2-hexanoyloxy-4-nitrobenzoic acid, 2-borneol and 3,5-dichlorosalicylaldehyde, as an off-white powder (yield 61.6%, calculated based on 2-hexanoyloxy-4-nitrobenzoic acid).
$^1$HNMR (500 MHZ, DMSO-d6) δ: 0.85-2.37 (m, 23H), 3.83 (s, 3H), 4.30 (s, 2H), 4.97 (s, 1H), 5.95 (s, 1H), 6.24-6.25 (dd, 1H), 7.10-7.11 (d, 1H), 7.14 (s, 1H), 7.39-7.40 (d, 1H), 7.54-7.56 (d, 1H). MS (M+H)$^+$: 562.2

Example 25 bornyl-2-methoxy-4-(2-hydroxy-3,5-dichlorobenzyl) amino-5-chlorobenzoate (ZL006-025)

With the method of Example 1, the title compound was synthesized with starting materials of 2-bornyl 2-methoxy-4-amino-5-chlorobenzoate and 3,5-dichlorosalicylaldehyde, as an off-white powder (yield 68.4%, calculated based on 2-bornyl 2-methoxy-4-amino-5-chlorobenzoate).
$^1$HNMR (300 MHz, DMSO-d6) δ: 0.85-2.05 (m, 16H), 3.83 (s, 3H), 4.31 (s, 2H), 4.97-4.99 (d, 1H), 5.94-5.95 (d, 1H), 6.26 (s, 1H), 7.09-7.10 (d, 1H), 7.14 (s, 1H), 7.38-7.39 (d, 1H), 7.56 (s, 1H). MS (M+H)$^+$: 512.1

Example 26 bornyl-2-methoxy-3-chloro-4-(2-hydroxy-3,5-dichlorobenzyl)aminobenzoate (ZL006-026)

With the method of Example 1, the title compound was synthesized with starting materials of 2-bornyl 2-methoxy-3-chloro-4-amino-5-chlorobenzoate and 3,5-dichlorosalicylaldehyde, as an off-white powder (yield 68.4%, calculated based on bornyl 2-methoxy-3-chloro-4-amino-5-chlorobenzoate).
$^1$HNMR (300 MHz, DMSO-d6) δ: 0.85-2.05 (m, 16H), 3.83 (s, 3H), 4.31 (s, 2H), 4.97-4.99 (d, 1H), 5.94-5.95 (d, 1H), 6.34-6.37 (d, 1H), 7.09-7.10 (d, 1H), 7.14 (s, 1H), 7.38-7.39 (d, 1H), 7.45-7.47 (d, 1H). MS (M+H)$^+$: 512.1

Example 27 bornyl-2-hydroxy-4-[N-(2-hydroxy-3,5-dichlorobenzyl)-N-methyl]aminobenzoate (ZL006-27)

With the method of Example 9, the title compound was synthesized with starting materials of bornyl-2-hydroxy-4-(2-hydroxy-3,5-dichlorobenzyl)aminobenzoate (ZL006-05), as an off-white powder (yield 73.4%, calculated based on bornyl-2-hydroxy-4-(2-hydroxy-3,5-dichlorobenzyl)aminobenzoate).
$^1$HNMR (300 MHz, DMSO-d6) δ: 0.85-2.05 (m, 16H), 3.06 (s, 3H), 4.31 (s, 2H), 4.97-4.99 (d, 1H), 5.94-5.95 (d, 1H), 6.23-6.25 (dd, 1H), 7.09-7.10 (d, 1H), 7.14 (s, 1H), 7.53-7.55 (d, 1H). MS (M+H)$^+$: 478.2

Example 28 bornyl-2-hydroxy-4-[N-(2-hydroxy-3,5-dichlorobenzyl)-N-acetyl]aminobenzoate (ZL006-28)

With the method of Example 10, the title compound was synthesized with starting materials of bornyl-2-hydroxy-4-(2-hydroxy-3,5-dichlorobenzyl)aminobenzoate (ZL006-05), as an off-white powder (yield 63.8%, calculated based on bornyl-2-hydroxy-4-(2-hydroxy-3,5-dichlorobenzyl)aminobenzoate).
$^1$HNMR (300 MHz, DMSO-d6) δ: 0.85-2.05 (m, 19H), 4.31 (s, 2H), 4.97-4.99 (d, 1H), 5.94-5.95 (d, 1H), 6.23-6.25 (dd, 1H), 7.09-7.10 (d, 1H), 7.14 (s, 1H), 7.53-7.55 (d, 1H). MS (M+H)$^+$: 506.1

Example 29 bornyl-2-methoxy-4-[N-(2-hydroxy-3,5-dichlorobenzyl)-N-methyl]aminobenzoate (ZL006-029)

With the method of Example 9, the title compound was synthesized with starting materials of bornyl-2-methoxy-4-(2-hydroxy-3,5-dichlorobenzyl)aminobenzoate (ZL006-020), as an off-white powder (yield 71.2%, calculated based on bornyl-2-methoxy-4-(2-hydroxy-3,5-dichlorobenzyl)aminobenzoate).
$^1$HNMR (300 MHz, DMSO-d6) δ: 0.85-2.05 (m, 16H), 3.06 (s, 3H), 3.83 (s, 3H), 4.31 (s, 2H), 4.97-4.99 (d, 1H), 5.94-5.95 (d, 1H), 6.23-6.25 (dd, 1H), 7.09-7.10 (d, 1H), 7.14 (s, 1H), 7.53-7.55 (d, 1H). MS (M+H)$^+$: 492.2

Example 30 bornyl-2-acetyloxy-4-[N-(2-hydroxy-3,5-dichlorobenzyl)-N-methyl]aminobenzoate (ZL006-030)

With the method of Example 9, the title compound was synthesized with starting materials of bornyl-2-acetyloxy-4-(2-hydroxy-3,5-dichlorobenzyl)aminobenzoate (ZL006-

06), as an off-white powder (yield 71.8%, calculated based on bornyl-2-acetyloxy-4-(2-hydroxy-3,5-dichlorobenzyl) aminobenzoate).

$^1$HNMR (500 MHZ, DMSO-d6) δ: 0.85-2.37 (m, 19H), 3.06 (s, 3H), 4.30 (s, 2H), 4.97 (s, 1H), 5.95 (s, 1H), 6.24-6.25 (dd, 1H), 7.10-7.11 (d, 1H), 7.14 (s, 1H), 7.54-7.56 (d, 1H). MS (M+H)$^+$: 520.2

Example 31 bornyl-2-acetyloxy-4-[N-(2-hydroxy-3,5-dichlorobenzyl)-N-acetyl]aminobenzoate (ZL006-031)

With the method of Example 10, the title compound was synthesized with starting materials of bornyl-2-acetyloxy-4-(2-hydroxy-3,5-dichlorobenzyl)aminobenzoate (ZL006-06), as an off-white powder (yield 72.1%, calculated based on bornyl-2-acetyloxy-4-(2-hydroxy-3,5-dichlorobenzyl) aminobenzoate).

$^1$HNMR (500 MHZ, DMSO-d6) δ: 0.85-2.37 (m, 22H), 4.30 (s, 2H), 4.97 (s, 1H), 5.95 (s, 1H), 6.24-6.25 (dd, 1H), 7.10-7.11 (d, 1H), 7.14 (s, 1H), 7.39-7.40 (d, 1H), 7.54-7.56 (d, 1H). MS (M+H)$^+$: 576.2

Example 32 bornyl-2-(2-methoxy-2-carbonylethoxy)-4-(2-hydroxy-3,5-dichlorobenzyl)aminobenzoate (ZL006-032)

With the method of Example 1, the title compound was synthesized with starting materials of bornyl-2-(2-methoxy-2-carbonylethoxy)-4-aminobenzoate and 3,5-dichlorosalicylaldehyde, as an off-white powder (yield 72.1%, calculated based on bornyl-2-(2-methoxy-2-carbonylethoxy)-4-aminobenzoate).

$^1$HNMR (500 MHZ, DMSO-d6) δ: 0.85-2.37 (m, 16H), 2.18 (s, 3H), 3.68 (s, 2H), 4.30 (s, 2H), 4.95 (s, 1H), 4.97 (s, 1H), 5.95 (s, 1H), 6.24-6.25 (dd, 1H), 7.10-7.11 (d, 1H), 7.14 (s, 1H), 7.39-7.40 (d, 1H), 7.54-7.56 (d, 1H). MS (M+H)$^+$: 536.2

Example 33 methyl 2-(bornyl-2-carbonylethoxy)-4-(2-hydroxy-3,5-dichlorobenzyl)aminobenzoate (ZL006-033)

With the method of Example 1, the title compound was synthesized with starting materials of methyl 2-(bornyl-2-carbonylethoxy)-4-aminobenzoate and 3,5-dichlorosalicylaldehyde, as an off-white powder (yield 72.3%, calculated based on methyl 2-(bornyl-2-carbonylethoxy)-4-aminobenzoate).

$^1$HNMR (500 MHZ, DMSO-d6) δ: 0.85-2.37 (m, 16H), 2.18 (s, 3H), 3.68 (s, 2H), 4.30 (s, 2H), 4.95 (s, 1H), 4.97 (s, 1H), 5.95 (s, 1H), 6.24-6.25 (dd, 1H), 7.10-7.11 (d, 1H), 7.14 (s, 1H), 7.39-7.40 (d, 1H), 7.54-7.56 (d, 1H), 10.88 (s, 1H). MS (M+H)$^+$: 536.2

Example 34 bornyl-2-(2-methoxy-2-carbonylethoxy)-4-[N-(2-hydroxy-3,5-dichlorobenzyl)-N-methyl]aminobenzoate (ZL006-034)

With the method of Example 9, the title compound was synthesized with starting materials of bornyl-2-(2-methoxy-2-carbonylethoxy)-4-(2-hydroxy-3,5-dichlorobenzyl)aminobenzoate (ZL006-032), as an off-white powder (yield 64.6%, calculated based on bornyl-2-(2-methoxy-2-carbonylethoxy)-4-(2-hydroxy-3,5-dichlorobenzyl) aminobenzoate).

$^1$HNMR (500 MHZ, DMSO-d6) δ: 0.85-2.37 (m, 16H), 2.18 (s, 3H), 3.06 (s, 3H), 3.68 (s, 2H), 4.30 (s, 2H), 4.95 (s, 1H), 4.97 (s, 1H), 5.95 (s, 1H), 6.24-6.25 (dd, 1H), 7.10-7.11 (d, 1H), 7.14 (s, 1H), 7.39-7.40 (d, 1H), 7.54-7.56 (d, 1H), 10.88 (s, 1H). MS (M+H)$^+$: 550.2

Example 35 methyl 2-(bornyl-2-carbonylethoxy)-4-[N-(2-hydroxy-3,5-dichlorobenzyl)-N-acetyl]aminobenzoate (ZL006-035)

With the method of Example 10, the title compound was synthesized with starting materials of methyl 2-(2-borny-2-carbonylethoxy)-4-(2-hydroxy-3,5-dichlorobenzyl)aminobenzoate (ZL006-033), as an off-white powder (yield 72.8%, calculated based on methyl 2-(bornyl-2-carbonylethoxy)-4-(2-hydroxy-3,5-dichlorobenzyl)aminobenzoate).

$^1$HNMR (500 MHZ, DMSO-d6) δ: 0.85-2.37 (m, 22H), 3.68 (s, 2H), 4.30 (s, 2H), 4.95 (s, 1H), 4.97 (s, 1H), 5.95 (s, 1H), 6.24-6.25 (dd, 1H), 7.10-7.11 (d, 1H), 7.14 (s, 1H), 7.39-7.40 (d, 1H), 7.54-7.56 (d, 1H), 10.88 (s, 1H). MS (M+H)$^+$: 578.2

Example 36 bornyl-2-(2-ethoxy-2-carbonylethoxy)-4-[N-(2-hydroxy-3,5-dichlorobenzyl)-N-(2-ethoxy-2-carbonylethyl)]aminobenzoate (ZL006-036)

bornyl-2-hydroxy-4-(2-hydroxy-3,5-dichlorobenzyl) aminobenzoate 5.05 g (0.01 mol) was poured into a 50 mL eggplant-shaped flask. To the flask was added 2 g fine powder of potassium carbonate ground by a mortar, 20 mL solution of dichloromethane, then ethyl bromoacetate 4.98 g (0.03 mol) was added dropwise with stirring. The reaction was refluxed for 8 h, then stopped, slightly cooled and filtered to remove inorganic salts, and the filtrate was concentrated to sandish material, purified by column chromatography with an eluant (petroleum ether:ethyl acetate (v/v)=20:1) to give a white crystalline powder (3.17 g, 49.8%).

$^1$HNMR (300 MHz, CDCl$_3$) δ: 0.85-2.05 (m, 22H), 4.21-4.31 (m, 4H), 4.50 (s, 2H), 4.72 (s, 2H), 4.78 (s, 2H), 6.08-6.09 (d, 1H), 6.14-6.17 (dd, 1H), 7.20-7.21 (d, 1H), 7.29-7.30 (d, 1H), 7.67-7.71 (d, 1H). MS (M+H)$^+$: 636.2

Example 37 bornyl-2-(bornyl-2-carbonylethoxy)-4-[N-(2-hydroxy-3,5-dichlorobenzyl)-N-(bornyl-2-carbonylethyl)]aminobenzoate (ZL006-037)

With the method of Example 36, the title compound was synthesized with starting materials of bornyl-2-hydroxy-4-(2-hydroxy-3,5-dichlorobenzyl)aminobenzoate and bornyl-bromoacetate, as an off-white powder (yield 48.2%, calculated based on bornyl-2-hydroxy-4-(2-hydroxy-3,5-dichlorobenzyl)aminobenzoate).

$^1$HNMR (300 MHz, CDCl$_3$) δ: 0.85-2.05 (m, 48H), 4.21-4.31 (m, 4H), 4.51 (s, 2H), 4.73 (s, 2H), 4.79 (s, 2H), 6.08-6.09 (d, 1H), 6.14-6.17 (dd, 1H), 7.20-7.21 (d, 1H), 7.29-7.30 (d, 1H), 7.67-7.71 (d, 1H). MS (M+H)$^+$: 730.3.

Example 38 methyl 2-acetyloxy-4-[N-(2-hydroxy-3,5-dichlorobenzyl)-N-(bornyl-2-carbonylethyl)]aminobenzoate (ZL006-38)

With the method of Example 1, methyl 2-acetyloxy-4-(2-hydroxy-3,5-dichlorobenzyl)aminobenzoate was synthesized with starting materials of ethyl 2-acetyloxy-4-aminobenzoate and 3,5-dichlorosalicylaldehyde.

With the method of Example 36, methyl 2-hydroxy-4-[N-(2-hydroxy-3,5-dichlorobenzyl)-(bornyl-acetate)]aminobenzoate (ZL006-38) was synthesized with starting materials of methyl 2-acetyloxy-4-(2-hydroxy-3,5-dichlorobenzyl)aminobenzoate, as an off-white powder (yield 47.9%, calculated based on methyl 2-acetyloxy-4-(2-hydroxy-3,5-dichlorobenzyl)aminobenzoate).

$^1$HNMR (500 MHz DMSO-d6) δ: 1.26-1.30 (t, 3H), 3.11 (s, 3H), 3.68 (s, 3H), 4.26 (q, 2H), 4.30 (d, 2H), 5.94-5.95 (d, 1H), 6.21-6.23 (dd, 1H), 7.11-7.16 (m, 2H), 7.48-7.51 (d, 1H), 9.79 (s, 1H). MS (M+H)$^+$: 730.3

Example 39 bornyl-2-hydroxy-4-(2-hydroxy-3-chloro-5-bromobenzyl) aminobenzoate (ZL006-039)

With the method of Example 1, the title compound was synthesized with starting materials of 4-nitrosalicylic acid, 2-borneol and 3-chloro-5-bromosalicylaldehyde, as an off-white powder (yield 22.6%, calculated based on 4-nitrosalicylic acid).

$^1$HNMR (300 MHz, DMSO-d6) δ: 0.85-2.05 (m, 16H), 4.31 (s, 2H), 4.97-4.99 (d, 1H), 5.94-5.95 (d, 1H), 6.23-6.25 (dd, 1H), 7.09-7.10 (t, 1H), 7.45-7.46 (d, 1H), 7.48-7.49 (d, 1H), 7.53-7.55 (d, 1H). MS (M+H)$^+$: 510.2

Example 40 bornyl-2-hydroxy-5-(2-hydroxy-3-chloro-5-bromobenzyl) aminobenzoate (ZL006-040)

With the method of Example 1, the title compound was synthesized with starting materials of 4-nitrosalicylic acid, 2-borneol and 3-chloro-5-bromosalicylaldehyde, as an off-white powder (yield 22.8%, calculated based on 4-nitrosalicylic acid).

$^1$HNMR (500 MHz, DMSO-d6) δ: 0.71-2.30 (m, 16H), 4.21 (s, 2H), 4.69-4.91 (m, 1H), 6.12 (s, 1H), 6.67-6.68 (d, 1H), 6.80-6.82 (dd, 1H), 6.92-6.94 (d, 1H), 7.44-7.45 (d, 1H), 7.46-7.47 (d, 1H). 9.79 (s, 1H). MS (M+H)$^+$: 510.2

Example 41 bornyl-2-methoxy-4-(2-hydroxy-3-chloro-5-bromobenzyl) aminobenzoate (ZL006-041)

With the method of Example 1, the title compound was synthesized with starting materials of 4-nitrosalicylic acid, 2-borneol and 2-methoxy-3-chloro-5-bromobenzaldehyde, as an off-white powder (yield 22.5%, calculated based on 4-nitrosalicylic acid).

$^1$HNMR (300 MHz, DMSO-d6) δ: 0.85-2.05 (m, 16H), 3.83 (s, 3H), 4.31 (s, 2H), 4.97-4.99 (d, 1H), 5.94-5.95 (d, 1H), 6.23-6.25 (dd, 1H), 7.09-7.10 (d, 1H), 7.46 (s, 1H), 7.48 (s, 1H), 7.53-7.55 (d, 1H). MS (M+H)$^+$: 524.1

Example 42 bornyl-2-n-butoxy-4-(2-hydroxy-3-chloro-5-bromobenzyl) aminobenzoate (ZL006-042)

With the method of Example 1, the title compound was synthesized with starting materials of 4-nitrosalicylic acid, 2-borneol and 2-n-butoxy-3-chloro-5-bromobenzaldehyde, as an off-white powder (yield 22.6%, calculated based on 4-nitrosalicylic acid).

$^1$HNMR (300 MHz, DMSO-d6) δ: 0.85-2.05 (m, 23H), 4.05-4.07 (t, 2H), 4.31 (s, 2H), 4.97-4.99 (d, 1H), 5.94-5.95 (d, 1H), 6.23-6.25 (dd, 1H), 7.09-7.10 (d, 1H), 7.46 (s, 1H), 7.48 (s, 1H), 7.53-7.55 (d, 1H), MS (M+H)$^+$: 566.1.

Example 43 bornyl-2-acetyloxy-4-(2-hydroxy-3-chloro-5-bromobenzyl) aminobenzoate (ZL006-43)

With the method of Example 1, the title compound was synthesized with starting materials of 2-acetyloxy-4-nitrobenzoic acid, 2-borneol and 3-chloro-5-bromosalicylaldehyde, as an off-white powder (yield 21.8%, calculated based on 2-acetyloxy-4-nitrosalicylic acid).

$^1$HNMR (500 MHZ, DMSO-d6) δ: 0.85-2.37 (m, 16H), 2.18 (s, 3H), 4.30 (s, 2H), 4.97 (s, 1H), 5.95 (s, 1H), 6.24-6.25 (dd, 1H), 7.10-7.11 (d, 1H), 7.46 (s, 1H), 7.48 (s, 1H), 7.54-7.56 (d, 1H), 9.76 (s, 1H). MS (M+H)$^+$: 552.10

Example 44 bornyl-2-butyryloxy-4-(2-hydroxy-3-chloro-5-bromobenzyl)aminobenzoate (ZL006-044)

With the method of Example 1, the title compound was synthesized with starting materials of 2-butyryloxy-4-nitrobenzoic acid, 2-borneol and 3-chloro-5-bromosalicylaldehyde, as an off-white powder (yield 22.3%, calculated based on 2-butyryloxy-4-nitrosalicylic acid).

$^1$HNMR (500 MHZ, DMSO-d6) δ: 0.85-2.37 (m, 23H), 4.30 (s, 2H), 4.97 (s, 1H), 5.95 (s, 1H), 6.24-6.25 (dd, 1H), 7.10-7.11 (d, 1H), 7.46 (s, 1H), 7.48 (s, 1H), 7.54-7.56 (d, 1H), 9.76 (s, 1H). MS (M+H)$^+$: 580.1.

Example 45 bornyl-2-hydroxy-4-[N-(2-hydroxy-3-chloro-5-bromobenzyl)-N-methyl]aminobenzoate (ZL006-045)

With the method of Example 9, the title compound was synthesized with starting materials of bornyl-2-hydroxy-4-(2-hydroxy-3-chloro-5-bromobenzyl)aminobenzoate (ZL006-039), as an off-white powder (yield 71.0%, calculated based on bornyl-2-hydroxy-4-(2-hydroxy-3-chloro-5-bromobenzyl)aminobenzoate)

$^1$HNMR (500 MHz, DMSO-d6) δ: 0.71-2.30 (m, 16H), 3.06 (s, 3H), 4.21 (s, 2H), 4.69-4.91 (m, 1H), 6.12 (s, 1H), 6.67-6.68 (d, 1H), 6.80-6.82 (dd, 1H), 6.92-6.94 (d, 1H), 7.44-7.45 (d, 1H), 7.46-7.47 (d, 1H), 9.79 (s, 1H). MS (M+H)$^+$: 524.1.

Example 46 bornyl-2-hydroxy-4-[N-(2-hydroxy-3-chloro-5-bromobenzyl)-N-acetyl]aminobenzoate (ZL006-046)

With the method of Example 10, the title compound was synthesized with starting materials of bornyl-2-hydroxy-4-(2-hydroxy-3-chloro-5-bromobenzyl)aminobenzoate (ZL006-039), as an off-white powder (yield 72.2%, calculated based on bornyl-2-hydroxy-4-(2-hydroxy-3-chloro-5-bromobenzyl)aminobenzoate)

$^1$HNMR (500 MHz, DMSO-d6) δ: 0.71-2.30 (m, 19H), 4.21 (s, 2H), 4.69-4.91 (m, 1H), 6.12 (s, 1H), 6.67-6.68 (d, 1H), 6.80-6.82 (dd, 1H), 6.92-6.94 (d, 1H), 7.44-7.45 (d, 1H), 7.46-7.47 (d, 1H), 9.79 (s, 1H). MS (M+H)$^+$: 552.1.

Example 47 bornyl-2-hydroxy-4-(2-hydroxy-3-chloro-5-trifluoromethylbenzyl)aminobenzoate (ZL006-047)

With the method of Example 1, the title compound was synthesized with starting materials of 4-nitrosalicylic acid, 2-borneol and 3-chloro-5-trifluoromethylsalicylaldehyde, as an off-white powder (yield 22.8%, calculated based on 4-nitrosalicylic acid).

$^1$HNMR (300 MHz, DMSO-d6) δ: 0.85-2.05 (m, 16H), 4.31 (s, 2H), 4.97-4.99 (d, 1H), 5.94-5.95 (d, 1H), 6.23-6.25 (dd, 1H), 7.09-7.10 (t, 1H), 7.19-7.20 (d, 1H), 7.45-7.47 (d, 1H), 7.53-7.55 (d, 1H), 9.79 (s, 1H). MS (M+H)$^+$: 498.2.

Example 48 bornyl-2-hydroxy-5-(2-hydroxy-3-chloro-5-trifluoromethylbenzyl)aminobenzoate (ZL006-048)

With the method of Example 1, the title compound was synthesized with starting materials of 4-nitrosalicylic acid, 2-borneol and 3-chloro-5-trifluoromethylsalicylaldehyde, as an off-white powder (yield 22.6%, calculated based on 4-nitrosalicylic acid).

$^1$HNMR (500 MHz, DMSO-d6) δ: 0.71-2.30 (m, 16H), 4.21 (s, 2H), 4.69-4.91 (m, 1H), 6.12 (s, 1H), 6.67-6.68 (d, 1H), 6.80-6.82 (dd, 1H), 6.92-6.94 (d, 1H), 7.19-7.20 (d, 1H), 7.45-7.47 (d, 1H), 9.79 (s, 1H). MS (M+H)$^+$: 498.2.

Example 49 bornyl-2-methoxy-4-(2-hydroxy-3-chloro-5-trifluoromethylbenzyl)aminobenzoate (ZL006-049)

With the method of Example 1, the title compound was synthesized with starting materials of 4-nitrosalicylic acid, 2-borneol and 2-methoxy-3-chloro-5-trifluoromethylbenzaldehyde, as an off-white powder (yield 21.8%, calculated based on 4-nitrosalicylic acid).

$^1$HNMR (300 MHz, DMSO-d6) δ: 0.85-2.05 (m, 16H), 3.83 (s, 3H), 4.31 (s, 2H), 4.97-4.99 (d, 1H), 5.94-5.95 (d, 1H), 6.23-6.25 (dd, 1H), 7.09-7.10 (d, 1H), 7.19-7.20 (d, 1H), 7.45-7.47 (d, 1H), 7.53-7.55 (d, 1H). MS (M+H)$^+$: 512.2.

Example 50 bornyl-2-n-butoxy-4-(2-hydroxy-3-chloro-5-trifluoromethylbenzyl)aminobenzoate (ZL006-050)

With the method of Example 1, the title compound was synthesized with starting materials of 4-nitrosalicylic acid, 2-borneol and 2-n-butoxy-3-chloro-5-trifluoromethylbenzaldehyde, as an off-white powder (yield 22.2%, calculated based on 4-nitrosalicylic acid).

$^1$HNMR (300 MHz, DMSO-d6) δ: 0.85-2.05 (m, 23H), 4.05-4.07 (t, 2H), 4.31 (s, 2H), 4.97-4.99 (d, 1H), 5.94-5.95 (d, 1H), 6.23-6.25 (dd, 1H), 7.09-7.10 (d, 1H), 7.19-7.20 (d, 1H), 7.45-7.47 (d, 1H), 7.53-7.55 (d, 1H). MS (M+H)$^+$: 554.2.

Example 51 bornyl-2-acetyloxy-4-(2-hydroxy-3-chloro-5-trifluoromethylbenzyl)aminobenzoate (ZL006-51)

With the method of Example 1, the title compound was synthesized with starting materials of 2-acetyloxy-4-nitrobenzoic acid, 2-borneol and 3-chloro-5-trifluoromethylsalicylaldehyde, as an off-white powder (yield 22.1%, calculated based on 2-acetyloxy-4-nitrosalicylic acid).

$^1$HNMR (500 MHZ, DMSO-d6) δ: 0.85-2.37 (m, 16H), 2.18 (s, 3H), 4.30 (s, 2H), 4.97 (s, 1H), 5.95 (s, 1H), 6.24-6.25 (dd, 1H), 7.10-7.11 (d, 1H), 7.19-7.20 (d, 1H), 7.45-7.47 (d, 1H), 7.54-7.56 (d, 1H), 9.76 (s, 1H). MS (M+H)$^+$: 540.2.

Example 52 bornyl-2-butyryloxy-4-(2-hydroxy-3-chloro-5-trifluoromethylbenzyl)aminobenzoate (ZL006-052)

With the method of Example 1, the title compound was synthesized with starting materials of 2-butyryloxy-4-nitrobenzoic acid, 2-borneol and 3-chloro-5-trifluoromethylsalicylaldehyde, as an off-white powder (yield 22.3%, calculated based on 2-butyryloxy-4-nitrosalicylic acid).

$^1$HNMR (500 MHZ, DMSO-d6) δ: 0.85-2.37 (m, 23H), 4.30 (s, 2H), 4.97 (s, 1H), 5.95 (s, 1H), 6.24-6.25 (dd, 1H), 7.10-7.11 (d, 1H), 7.19-7.20 (d, 1H), 7.45-7.47 (d, 1H), 7.54-7.56 (d, 1H), 9.76 (s, 1H). MS (M+H)$^+$: 568.2.

Example 53 bornyl-2-hydroxy-4-[N-(2-hydroxy-3-chloro-5-trifluoromethylbenzyl)-N-methyl]aminobenzoate (ZL006-053)

With the method of Example 9, the title compound was synthesized with starting materials of bornyl-2-hydroxy-4-(2-hydroxy-3-chloro-5-trifluoromethylbenzyl)aminobenzoate (ZL006-047), as an off-white powder (yield 71.1%, calculated based on bornyl-2-hydroxy-4-(2-hydroxy-3-chloro-5-trifluoromethylbenzyl)aminobenzoate).

$^1$HNMR (500 MHz, DMSO-d6) δ: 0.71-2.30 (m, 16H), 3.06 (s, 3H), 4.21 (s, 2H), 4.69-4.91 (m, 1H), 6.12 (s, 1H), 6.67-6.68 (d, 1H), 6.80-6.82 (dd, 1H), 6.92-6.94 (d, 1H), 7.19-7.20 (d, 1H), 7.45-7.47 (d, 1H), 9.79 (s, 1H). MS (M+H)+: 512.2.

Example 54 bornyl-2-hydroxy-4-[N-(2-hydroxy-3-chloro-5-trifluoromethylbenzyl)-N-acetyl]aminobenzoate (ZL006-054)

With the method of Example 10, the title compound was synthesized with starting materials of bornyl 2-hydroxy-4-(2-hydroxy-3-chloro-5-trifluoromethylbenzyl)aminobenzoate (ZL006-047), as an off-white powder (yield 72.7%, calculated based on bornyl-2-hydroxy-4-(2-hydroxy-3-chloro-5-trifluoromethylbenzyl)aminobenzoate).

$^1$HNMR (500 MHz, DMSO-d6) δ: 0.71-2.30 (m, 19H), 4.21 (s, 2H), 4.69-4.91 (m, 1H), 6.12 (s, 1H), 6.67-6.68 (d, 1H), 6.80-6.82 (dd, 1H), 6.92-6.94 (d, 1H), 7.19-7.20 (d, 1H), 7.45-7.47 (d, 1H), 9.79 (s, 1H). MS (M+H)+: 540.2.

Example 55 bornyl-2-hydroxy-4-(2-hydroxy-3-chloro-5-fluorobenzyl) aminobenzoate (ZL006-055)

With the method of Example 1, the title compound was synthesized with starting materials of 4-nitrosalicylic acid, 2-borneol and 3-chloro-5-fluorosalicylaldehyde, as an off-white powder (yield 22.4%, calculated based on 4-nitrosalicylic acid).

$^1$HNMR (300 MHz, DMSO-d6) δ: 0.85-2.05 (m, 16H), 4.31 (s, 2H), 4.97-4.99 (d, 1H), 5.94-5.95 (d, 1H), 6.23-6.25 (dd, 1H), 6.47-6.49 (d, 1H), 7.09-7.10 (1, 1H), 7.47-7.49 (d, 1H), 7.53-7.55 (d, 1H), 9.79 (s, 1H). MS (M+H)+: 448.2.

Example 56 bornyl-2-hydroxy-5-(2-hydroxy-3-chloro-5-fluorobenzyl)aminobenzoate (ZL006-056)

With the method of Example 1, the title compound was synthesized with starting materials of 4-nitrosalicylic acid, 2-borneol and 3-chloro-5-fluorosalicylaldehyde, as an off-white powder (yield 22.1%, calculated based on 4-nitrosalicylic acid).

$^1$HNMR (500 MHz, DMSO-d6) δ: 0.71-2.30 (m, 16H), 4.21 (s, 2H), 4.69-4.91 (m, 1H), 6.12 (s, 1H), 6.47-6.49 (d, 1H), 6.67-6.68 (d, 1H), 6.80-6.82 (dd, 1H), 6.92-6.94 (d, 1H), 7.19-7.20 (d, 1H), 7.47-7.49 (d, 1H), 9.79 (s, 1H). MS (M+H)+: 448.2.

Example 57 bornyl-2-methoxy-4-(2-hydroxy-3-chloro-5-fluorobenzyl) aminobenzoate (ZL006-057)

With the method of Example 1, the title compound was synthesized with starting materials of 4-nitrosalicylic acid, 2-borneol and 2-methoxy-3-chloro-5-fluorobenzaldehyde, as an off-white powder (yield 22.6%, calculated based on 4-nitrosalicylic acid).

$^1$HNMR (300 MHz, DMSO-d6) δ: 0.85-2.05 (m, 16H), 3.83 (s, 3H), 4.31 (s, 2H), 4.97-4.99 (d, 1H), 5.94-5.95 (d, 1H), 6.23-6.25 (dd, 1H), 6.47-6.49 (d, 1H), 7.09-7.10 (d, 1H), 7.19-7.20 (d, 1H), 7.47-7.49 (d, 1H), 9.79 (s, 1H). MS (M+H)+: 462.2.

Example 58 bornyl-2-n-butoxy-4-(2-hydroxy-3-chloro-5-fluorobenzyl) aminobenzoate (ZL006-058)

With the method of Example 1, the title compound was synthesized with starting materials of 4-nitrosalicylic acid, 2-borneol and 2-n-butoxy-3-chloro-5-fluorobenzaldehyde, as an off-white powder (yield 22.3%, calculated based on 4-nitrosalicylic acid).

$^1$HNMR (300 MHz, DMSO-d6) δ: 0.85-2.05 (m, 23H), 4.05-4.07 (t, 2H), 4.31 (s, 2H), 4.97-4.99 (d, 1H), 5.94-5.95 (d, 1H), 6.23-6.25 (dd, 1H), 6.47-6.49 (d, 1H), 7.09-7.10 (d, 1H), 7.19-7.20 (d, 1H), 7.47-7.49 (d, 1H), 9.79 (s, 1H). MS (M+H)+: 504.2.

Example 59 bornyl-2-acetyloxy-4-(2-hydroxy-3-chloro-5-fluorobenzyl) aminobenzoate (ZL006-59)

With the method of Example 1, the title compound was synthesized with starting materials of 2-acetyloxy-4-nitrobenzoic acid, 2-borneol and 3-chloro-5-fluorosalicylaldehyde, as an off-white powder (yield 21.9%, calculated based on 2-acetyloxy-4-nitrosalicylic acid).

$^1$HNMR (500 MHZ, DMSO-d6) δ: 0.85-2.37 (m, 16H), 2.18 (s, 3H), 4.30 (s, 2H), 4.97 (s, 1H), 5.95 (s, 1H), 6.24-6.25 (dd, 1H), 6.47-6.49 (d, 1H), 7.10-7.11 (d, 1H), 7.19-7.20 (d, 1H), 7.47-7.49 (d, 1H), 9.76 (s, 1H). MS (M+H)+: 490.2.

Example 60 bornyl-2-butyryloxy-4-(2-hydroxy-3-chloro-5-fluorobenzyl)aminobenzoate (ZL006-060)

With the method of Example 1, the title compound was synthesized with starting materials of 2-butyryloxy-4-nitrobenzoic acid, 2-borneol and 3-chloro-5-fluorosalicylaldehyde, as an off-white powder (yield 21.8%, calculated based on 2-butyryloxy-4-nitrosalicylic acid).

$^1$HNMR (500 MHZ, DMSO-d6) δ: 0.85-2.37 (m, 23H), 4.30 (s, 2H), 4.97 (s, 1H), 5.95 (s, 1H), 6.24-6.25 (dd, 1H), 6.47-6.49 (d, 1H), 7.10-7.11 (d, 1H), 7.19-7.20 (d, 1H), 7.47-7.49 (d, 1H), 9.76 (s, 1H). MS (M+H)+: 518.2.

Example 61 bornyl-2-hydroxy-4-[N-(2-hydroxy-3-chloro-5-fluorobenzyl)-N-methyl]aminobenzoate (ZL006-061)

With the method of Example 9, the title compound was synthesized with starting materials of bornyl-2-hydroxy-4-(2-hydroxy-3-chloro-5-fluorobenzyl)aminobenzoate (ZL006-055), as an off-white powder (yield 71.1%, calculated based on bornyl-2-hydroxy-4-(2-hydroxy-3-chloro-5-fluorobenzyl)aminobenzoate).

$^1$HNMR (500 MHz, DMSO-d6) δ: 0.71-2.30 (m, 16H), 3.06 (s, 3H), 4.21 (s, 2H), 4.69-4.91 (m, 1H), 6.12 (s, 1H), 6.47-6.49 (d, 1H), 6.67-6.68 (d, 1H), 6.80-6.82 (dd, 1H), 6.92-6.94 (d, 1H), 7.19-7.20 (d, 1H), 7.47-7.49 (d, 1H), 9.79 (s, 1H). MS (M+H)+: 462.2.

Example 62 bornyl-2-hydroxy-4-[N-(2-hydroxy-3-chloro-5-fluorobenzyl)-N-acetyl]aminobenzoate (ZL006-062)

With the method of Example 10, the title compound was synthesized with starting materials of bornyl-2-hydroxy-4-(2-hydroxy-3-chloro-5-fluorobenzyl)aminobenzoate (ZL006-055), as an off-white powder (yield 72.4%, calculated based on bornyl-2-hydroxy-4-(2-hydroxy-3-chloro-5-fluorobenzyl)aminobenzoate).

$^1$HNMR (500 MHz, DMSO-d6) δ: 0.71-2.30 (m, 19H), 4.21 (s, 2H), 4.69-4.91 (m, 1H), 6.12 (s, 1H), 6.47-6.49 (d, 1H), 6.67-6.68 (d, 1H), 6.80-6.82 (dd, 1H), 6.92-6.94 (d, 1H), 7.19-7.20 (d, 1H), 7.47-7.49 (d, 1H), 9.79 (s, 1H). MS (M+H)$^+$: 490.2.

Example 63 bornyl-2-hydroxy-4-(2-hydroxy-5-bromobenzyl)aminobenzoate (ZL006-063)

With the method of Example 1, the title compound was synthesized with starting materials of 4-nitrosalicylic acid, 2-borneol and 5-bromosalicylaldehyde, as an off-white powder (yield 21.4%, calculated based on 4-nitrosalicylic acid).

$^1$HNMR (300 MHz, DMSO-d6) δ: 0.85-2.05 (m, 16H), 3.14-3.16 (m, 1H), 4.27 (s, 2H), 5.95 (s, 1H), 6.21-6.23 (dd, 1H), 6.78-6.79 (d, 1H), 7.11 (s, 1H), 7.21-7.22 (d, 2H), 7.47-7.49 (d, 1H), 9.98 (s, 1H), 10.89 (s, 1H). MS (M+H)$^+$: 510.1.

Example 64 bornyl-2-methoxy-4-(2-hydroxy-5-bromobenzyl)aminobenzoate (ZL006-064)

With the method of Example 1, the title compound was synthesized with starting materials of 4-nitrosalicylic acid, 2-borneol and 2-methoxy-5-bromobenzaldehyde, as an off-white powder (yield 22.6%, calculated based on 4-nitrosalicylic acid).

$^1$HNMR (300 MHz, DMSO-d6) δ: 0.85-2.05 (m, 16H), 3.83 (s, 3H), 4.31 (s, 2H), 4.97-4.99 (d, 1H), 5.95 (s, 1H), 6.21-6.23 (dd, 1H), 6.78-6.79 (d, 1H), 7.11 (s, 1H), 7.21-7.22 (d, 2H), 7.47-7.49 (d, 1H), 9.98 (s, 1H), 10.89 (s, 1H). MS (M+H)$^+$: 524.1.

Example 65 bornyl-2-acetyloxy-4-(2-hydroxy-5-bromobenzyl)aminobenzoate (ZL006-65)

With the method of Example 1, the title compound was synthesized with starting materials of 2-acetyloxy-4-nitrobenzoic acid, 2-borneol and 5-bromosalicylaldehyde, as an off-white powder (yield 22.6%, calculated based on 2-acetyloxy-4-nitrosalicylic acid).

$^1$HNMR (500 MHZ, DMSO-d6) δ: 0.85-2.37 (m, 16H), 2.18 (s, 3H), 4.30 (s, 2H), 4.97 (s, 1H), 5.95 (s, 1H), 6.21-6.23 (dd, 1H), 6.78-6.79 (d, 1H), 7.11 (s, 1H), 7.21-7.22 (d, 2H), 7.47-7.49 (d, 1H), 9.98 (s, 1H), 10.89 (s, 1H). MS (M+H)$^+$: 552.1.

Example 66 bornyl-2-hydroxy-4-(2-hydroxy-5-chlorobenzyl)aminobenzoate (ZL006-066)

With the method of Example 1, the title compound was synthesized with starting materials of 4-nitrosalicylic acid, 2-borneol and 5-chlorosalicylaldehyde, as an off-white powder (yield 22.3%, calculated based on 4-nitrosalicylic acid).

$^1$HNMR (300 MHz, DMSO-d6) δ: 0.73-1.82 (m, 16H), 4.17 (s, 2H), 4.64-4.66 (d, 1H), 6.47 (s, 1H), 6.82-6.84 (d, 2H), 6.89-6.92 (d, 1H), 6.94-6.95 (d, 1H), 7.07-7.09 (d, 2H), 9.98 (s, 1H), 10.89 (s, 1H). MS (M+H)$^+$: 430.2.

Example 67 bornyl-2-methoxy-4-(2-hydroxy-5-chlorobenzyl)aminobenzoate (ZL006-067)

With the method of Example 1, the title compound was synthesized with starting materials of 4-nitrosalicylic acid, 2-borneol and 2-methoxy-5-chlorobenzaldehyde, as an off-white powder (yield 21.8%, calculated based on 4-nitrosalicylic acid).

$^1$HNMR (300 MHz, DMSO-d6) δ: 0.73-1.82 (m, 16H), 3.83 (s, 3H), 4.17 (s, 2H), 4.64-4.66 (d, 1H), 6.47 (s, 1H), 6.82-6.84 (d, 2H), 6.89-6.92 (d, 1H), 6.94-6.95 (d, 1H), 7.07-7.09 (d, 2H). MS (M+H)$^+$: 444.2.

Example 68 bornyl-2-acetyloxy-4-(2-hydroxy-5-chlorobenzyl)aminobenzoate (ZL006-68)

With the method of Example 1, the title compound was synthesized with starting materials of 2-acetyloxy-4-nitrobenzoic acid, 2-borneol and 5-chlorosalicylaldehyde, as an off-white powder (yield 21.9%, calculated based on 2-acetyloxy-4-nitrosalicylic acid).

$^1$HNMR (300 MHz, DMSO-d6) δ: 0.73-1.82 (m, 16H), 2.18 (s, 3H), 4.17 (s, 2H), 4.64-4.66 (d, 1H), 6.47 (s, 1H), 6.82-6.84 (d, 2H), 6.89-6.92 (d, 1H), 6.94-6.95 (d, 1H), 7.07-7.09 (d, 2H). MS (M+H)$^+$: 472.2.

Example 69 bornyl-2-hydroxy-4-(2-hydroxy-5-fluorobenzyl)aminobenzoate (ZL006-069)

With the method of Example 1, the title compound was synthesized with starting materials of 4-nitrosalicylic acid, 2-borneol and 5-fluorosalicylaldehyde, as an off-white powder (yield 22.1%, calculated based on 4-nitrosalicylic acid).

$^1$HNMR (300 MHz, DMSO-d6) δ: 0.74-1.99 (m, 16H), 4.21 (s, 2H), 4.89-4.92 (d, 1H), 6.49 (s, 1H), 6.76-6.77 (d, 1H), 6.79-6.82 (d, 1H), 6.83-6.87 (d, 1H), 6.88-6.92 (dd, 1H), 6.94-6.95 (d, 1H), 7.07-7.08 (d, 1H), 9.54 (s, 1H). MS (M+H)$^+$: 414.2.

Example 70 bornyl-2-methoxy-4-(2-hydroxy-5-fluorobenzyl)aminobenzoate (ZL006-070)

With the method of Example 1, the title compound was synthesized with starting materials of 4-nitrosalicylic acid, 2-borneol and 2-methoxy-5-fluorobenzaldehyde, as an off-white powder (yield 22.5%, calculated based on 4-nitrosalicylic acid).

$^1$HNMR (300 MHz, DMSO-d6) δ: 0.74-1.99 (m, 16H), 3.83 (s, 3H), 4.21 (s, 2H), 4.89-4.92 (d, 1H), 6.49 (s, 1H), 6.76-6.77 (d, 1H), 6.79-6.82 (d, 1H), 6.83-6.87 (d, 1H), 6.88-6.92 (dd, 1H), 6.94-6.95 (d, 1H), 7.07-7.08 (d, 1H), 9.54 (s, 1H). MS (M+H)$^+$: 428.20

Example 71 bornyl-2-acetyloxy-4-(2-hydroxy-5-fluorobenzyl) aminobenzoate (ZL006-071)

With the method of Example 1, the title compound was synthesized with starting materials of 2-acetyloxy-4-nitrobenzoic acid, 2-borneol and 5-fluorosalicylaldehyde, as an off-white powder (yield 22.3%, calculated based on 2-acetyloxy-4-nitrosalicylic acid).

$^1$HNMR (300 MHz, DMSO-d6) δ: 0.74-1.99 (m, 16H), 2.29 (s, 3H), 4.21 (s, 2H), 4.89-4.92 (d, 1H), 6.49 (s, 1H), 6.76-6.77 (d, 1H), 6.79-6.82 (d, 1H), 6.83-6.87 (d, 1H), 6.88-6.92 (dd, 1H), 6.94-6.95 (d, 1H), 7.07-7.08 (d, 1H), 9.54 (s, 1H). MS (M+H)$^+$: 456.20

Example 72 bornyl-2-hydroxy-4-(2-hydroxy-5-trifluoromethylbenzyl) aminobenzoate (ZL006-072)

With the method of Example 1, the title compound was synthesized with starting materials of 4-nitrosalicylic acid, 2-borneol and 5-trifluoromethylsalicylaldehyde, as an off-white powder (yield 22.0%, calculated based on 4-nitrosalicylic acid).

$^1$HNMR (300 MHz, DMSO-d6) δ: 0.85-2.05 (m, 16H), 3.14-3.16 (m, 1H), 4.27 (s, 2H), 5.95 (s, 1H), 6.21-6.23 (dd, 1H), 6.78-6.79 (d, 1H), 7.11 (s, 1H), 7.25-7.27 (s, 1H), 7.31-7.33 (d, 1H), 7.47-7.49 (d, 1H), 9.98 (s, 1H), 10.89 (s, 1H). MS (M+H)$^+$: 464.2.

Example 73 bornyl-2-methoxy-4-(2-hydroxy-5-trifluoromethylbenzyl) aminobenzoate (ZL006-073)

With the method of Example 1, the title compound was synthesized with starting materials of 4-nitrosalicylic acid, 2-borneol and 2-methoxy-5-trifluoromethylbenzaldehyde, as an off-white powder (yield 22.1%, calculated based on 4-nitrosalicylic acid).

$^1$HNMR (300 MHz, DMSO-d6) δ: 0.85-2.05 (m, 16H), 3.14-3.16 (m, 1H), 3.83 (s, 3H), 4.27 (s, 2H), 5.95 (s, 1H), 6.21-6.23 (dd, 1H), 6.78-6.79 (d, 1H), 7.11 (s, 1H), 7.25-7.27 (s, 1H), 7.31-7.33 (d, 1H), 7.47-7.49 (d, 1H), 9.98 (s, 1H). MS (M+H)$^+$: 478.2.

Example 74 bornyl-2-acetyloxy-4-(2-hydroxy-5-trifluoromethylbenzyl)aminobenzoate (ZL006-074)

With the method of Example 1, the title compound was synthesized with starting materials of 2-acetyloxy-4-nitrobenzoic acid, 2-borneol and 5-trifluoromethylsalicylaldehyde, as an off-white powder (yield 21.7%, calculated based on 2-acetyloxy-4-nitrosalicylic acid).

$^1$HNMR (300 MHz, DMSO-d6) δ: 0.85-2.05 (m, 16H), 2.18 (s, 3H), 3.14-3.16 (m, 1H), 4.27 (s, 2H), 5.95 (s, 1H), 6.21-6.23 (dd, 1H), 6.78-6.79 (d, 1H), 7.11 (s, 1H), 7.25-7.27 (s, 1H), 7.31-7.33 (d, 1H), 7.47-7.49 (d, 1H), 9.98 (s, 1H). MS (M+H)$^+$: 506.2.

Example 75 bornyl-2-hydroxy-4-(2-methoxy-3,5-dichlorobenzyl) aminobenzoate (ZL006-075)

With the method of Example 1, the title compound was synthesized with starting materials of 4-nitrosalicylic acid, 2-borneol and 2-methoxy-3,5-dichlorobenzaldehyde, as an off-white powder (yield 21.8%, calculated based on 4-nitrosalicylic acid).

$^1$HNMR (300 MHz, DMSO-d6) δ: 0.85-2.05 (m, 16H), 3.83 (s, 3H), 4.31 (s, 2H), 4.97-4.99 (d, 1H), 5.94-5.95 (d, 1H), 6.23-6.25 (dd, 1H), 7.09-7.10 (d, 1H), 7.14 (s, 1H), 7.38-7.39 (d, 1H), 7.53-7.55 (d, 1H). MS (M+H)$^+$: 478.2.

Example 76 bornyl-2-hydroxy-4-(2-acetyloxy-3,5-dichlorobenzyl) aminobenzoate (ZL006-076)

With the method of Example 1, the title compound was synthesized with starting materials of 4-nitrosalicylic acid, 2-borneol and 2-acetyloxy-3,5-dichlorobenzaldehyde, as an off-white powder (yield 22.1%, calculated based on 4-nitrosalicylic acid).

$^1$HNMR (300 MHz, DMSO-d6) δ: 0.85-2.05 (m, 16H), 2.16 (s, 3H), 4.31 (s, 2H), 4.97-4.99 (d, 1H), 5.94-5.95 (d, 1H), 6.23-6.25 (dd, 1H), 7.09-7.10 (d, 1H), 7.14 (s, 1H), 7.38-7.39 (d, 1H), 7.53-7.55 (d, 1H). MS (M+H)$^+$: 506.1

Example 77 bornyl-2-hydroxy-4-(2-methoxy-3-chloro-5-bromobenzyl) aminobenzoate (ZL006-077)

With the method of Example 1, the title compound was synthesized with starting materials of 4-nitrosalicylic acid, 2-borneol and 2-methoxy-3-chloro-5-bromobenzaldehyde, as an off-white powder (yield 22.3%, calculated based on 4-nitrosalicylic acid).

$^1$HNMR (300 MHz, DMSO-d6) δ: 0.85-2.05 (m, 16H), 3.83 (s, 3H), 4.31 (s, 2H), 4.97-4.99 (d, 1H), 5.94-5.95 (d, 1H), 6.23-6.25 (dd, 1H), 7.09-7.10 (d, 1H), 7.45-7.46 (d, 1H), 7.48-7.49 (d, 1H), 7.53-7.55 (d, 1H). MS (M+H)$^+$: 524.1.

Example 78 bornyl-2-hydroxy-4-(2-acetyloxy-3-chloro-5-bromobenzyl) aminobenzoate (ZL006-078)

With the method of Example 1, the title compound was synthesized with starting materials of 4-nitrosalicylic acid, 2-borneol and 2-acetyloxy-3-chloro-5-bromobenzaldehyde, as an off-white powder (yield 22.1%, calculated based on 4-nitrosalicylic acid).

$^1$HNMR (300 MHz, DMSO-d6) δ: 0.85-2.05 (m, 16H), 2.16 (s, 3H), 4.31 (s, 2H), 4.97-4.99 (d, 1H), 5.94-5.95 (d, 1H), 6.23-6.25 (dd, 1H), 7.09-7.10 (d, 1H), 7.45-7.46 (d, 1H), 7.48-7.49 (d, 1H), 7.53-7.55 (d, 1H), MS (M+H)$^+$: 552.1

Example 79 bornyl-2-hydroxy-4-(2-methoxy-3-chloro-5-trifluoromethylbenzyl)aminobenzoate (ZL006-079)

With the method of Example 1, the title compound was synthesized with starting materials of 4-nitrosalicylic acid, 2-borneol and 2-methoxy-3-chloro-5-bromobenzaldehyde, as an off-white powder (yield 21.9%, calculated based on 4-nitrosalicylic acid).

$^1$HNMR (300 MHz, DMSO-d6) δ: 0.85-2.05 (m, 16H), 3.83 (s, 3H), 4.31 (s, 2H), 4.97-4.99 (d, 1H), 5.94-5.95 (d, 1H), 6.23-6.25 (dd, 1H), 7.09-7.10 (d, 1H), 7.19-7.20 (d, 1H), 7.45-7.46 (d, 1H), 7.53-7.55 (d, 1H). MS (M+H)$^+$: 512.2

Example 80 bornyl-2-hydroxy-4-(2-acetyloxy-3-chloro-5-trifluoromethylbenzyl)aminobenzoate (ZL006-080)

With the method of Example 1, the title compound was synthesized with starting materials of 4-nitrosalicylic acid, 2-borneol and 2-acetyloxy-3-chloro-5-bromobenzaldehyde, as an off-white powder (yield 22.1%, calculated based on 4-nitrosalicylic acid).

$^1$HNMR (300 MHz, DMSO-d6) δ: 0.85-2.05 (m, 16H), 2.16 (s, 3H), 4.31 (s, 2H), 4.97-4.99 (d, 1H), 5.94-5.95 (d, 1H), 6.23-6.25 (dd, 1H), 7.09-7.10 (d, 1H), 7.19-7.20 ((d, 1H) 7.46-7.47 (d, 1H), 7.53-7.55 (d, 1H). MS (M+H)$^+$: 540.2

Example 81 methyl 2-acetyloxy-4-[N-(2-hydroxy-3,5-dichlorobenzyl)-N-acetyl]aminobenzoate (ZL006-081)

With the method of Example 1, methyl 2-acetyloxy-4-[N-(2-hydroxy-3,5-dichlorobenzyl)]aminobenzoate was synthesized with starting materials of acetyloxy-4-nitrobenzoic acid and 3,5-dichlorosalicylaldehyde.

With the method of Example 10, 2-acetyloxy-4-[N-(2-hydroxy-3,5-dichlorobenzyl)-N-acetyl]aminobenzoate (ZL006-81) was synthesized with starting materials of methyl 2-acetyloxy-4-[N-(2-hydroxy-3,5-dichlorobenzyl)] aminobenzoate, as an off-white powder (yield 13.1%, calculated based on acetyloxy-4-nitrobenzoic acid).

$^1$HNMR (300 MHz, DMSO-6d) δ: 2.24 (s, 3H), 2.26 (s, 3H), 3.12 (s, 3H), 4.88 (s, 2H), 7.21-7.22 (d, 1H), 7.25 (s, 1H), 7.26-7.27 (d, 1H), 7.66-7.67 (d, 1H), 7.90-7.91 (d, 1H). MS (M+H)$^+$: 426.0

Example 82 methyl 2-acetyloxy-4-[N-(2-hydroxy-3-chloro-5-bromobenzyl)-N-acetyl]aminobenzoate (ZL006-82)

With the method of Example 1, methyl 2-acetyloxy-4-[N-(2-hydroxy-3,5-dichlorobenzyl)]aminobenzoate was synthesized with starting materials of acetyloxy-4-nitrobenzoic acid and 3-chloro-5-bromosalicylaldehyde.

With the method of Example 10, 2-acetyloxy-4-[N-(2-hydroxy-3-chloro-5-bromobenzyl)-N-acetyl]aminobenzoate (ZL006-82) was synthesized with starting materials of methyl 2-acetyloxy-4-[N-(2-hydroxy-3-chloro-5-bromobenzyl)]aminobenzoate, as an off-white powder (yield 13.3%, calculated based on acetyloxy-4-nitrobenzoic acid).

$^1$HNMR (300 MHz, DMSO-6d) δ: 2.24 (s, 3H), 2.26 (s, 3H), 3.15 (s, 3H), 4.31 (s, 2H), 4.97-4.99 (d, 1H), 5.94-5.95 (d, 1H), 6.23-6.25 (d, 1H), 7.09-7.10 (d, 1H), 7.45-7.46 (d, 1H), 7.48-7.49 (d, 1H), 7.54-7.56 (d, 1H). MS (M+H)$^+$: 472.0

Example 83 methyl 2-acetyloxy-4-[N-(2-hydroxy-3-chloro-5-trifluoromethylbenzyl)-N-acetyl]aminobenzoate (ZL006-83)

With the method of Example 1, methyl 2-acetyloxy-4-[N-(2-hydroxy-3,5-dichlorobenzyl)]aminobenzoate was synthesized with starting materials of acetyloxy-4-nitrobenzoic acid and 3-chloro-5-trifluoromethylsalicylaldehyde.

With the method of Example 10, 2-acetyloxy-4-[N-(2-hydroxy-3-chloro-5-trifluoromethylbenzyl)-N-acetyl]aminobenzoate (ZL006-83) was synthesized with starting materials of methyl 2-acetyloxy-4-[N-(2-hydroxy-3-chloro-5-trifluoromethylbenzyl)]aminobenzoate, as an off-white powder (yield 13.0%, calculated based on acetyloxy-4-nitrobenzoic acid).

$^1$HNMR (300 MHz, DMSO-6d) δ: 2.24 (s, 3H), 2.26 (s, 3H), 3.13 (s, 3H), 4.32 (s, 2H), 4.98-4.99 (d, 1H), 5.95-5.96 (d, 1H), 6.23-6.25 (d, 1H), 7.19-7.20 (d, 1H), 7.46-7.47 (d, 1H), 7.54-7.55 (d, 1H), MS (M+H)$^+$: 460.1

Effects of objective compounds on the interaction between nNOS and PSD-95

Example 84

Culture of Primary Neurons

Neonatal mice within 24 h were disinfected successively with benzalkonium bromide solution and 75% ethanol, followed by the disinfection to head skin with povidone-iodine. The head was fixed by clamping the neck skin by left hand, while the skull was cut open with an ophthalmic tweezer by right hand, exposing two cerebral hemispheres. The two pieces of cerebral cortex was placed in Petri dishes containing D-Hank's solution; the meninges was removed. The prepared cerebral cortex was added into a 5 ml small beaker, cut into small pieces of tissue less than 1 mm$^3$ using ophthalmic scissors and the pieces of tissue were transferred to a 50 ml conical flask. The well-incubated 0.125% Trypsin solution was added into a 20 ml conical flask and mixed thoroughly. After the digestion for 10 min in an incubator (37° C.), the suspension was gently pipetted with a pipette until the absence of tissue pieces. The cell suspension was transferred to a 200-mesh sieve to filter, and the enzyme reaction of the filtrate was terminated by DMEM/F12 (1:1) medium containing 10% FBS. The filtrate was centrifuged (2500 rp, 3 min) and the supernatant was removed. Cells were resuspended with Neurobasal medium containing 2% B27, 0.5 mM L-glutamine, 5 IU penicillin and 5 μg/mL streptomycin by gently pipetting with a glass pipette having a smooth tip and seeded in Petri dishes coated with PORN (10 μg/ml), with a seeding density of 5×10 cells/cm$^2$. The cells were maintained under 5% CO$_2$, 37° C., and half the amount of Neurobasal medium was refreshed every 3-4 days.

Example 85

Co-Immunoprecipitation of nNOS with PSD-95

The culture solution in the Petri dishes was sucked out and the Petri dishes were washed with PBS for three times, to which was added appropriate amount of 100 mM HEMS containing 200 mM NaCl, 10% glycerol, 2 mM $NaO_4P_2O_7$, 2 mM DTT, 1 mM EDTA, 1 mM benzamidine, 0.1 mM $Na_3VO_4$, 1 μM pepstatine, 10 μg/mL aprotinine, 10 μg/mL leupeptin and 10 μM phenylmethylsulfonyl fluoride. The cells were scraped with a cell scraper, lysed on ice for 30 minutes, centrifuged at 12000×g, 4° C. for 15 min, and the supernatant was carefully collected as the protein extracts. 50 μl Protein G-Sepharose beads was washed twice with PBS, and resuspended with 50 μl PBS. nNOS antibody was added to the suspensions and shaken at 4° C. for 3-4 h. The supernatant of the extracted protein (either primary neuronal proteins or cortical tissue proteins) was added to the beads so that the final concentration of the nNOS antibody was 1:100. The protein-antibody-Beads were incubated at 4° C. overnight. Next day, the protein-antibody-Beads complex was washed with PBS repeatedly for three times, each time with 20 min shaking at 4° C. At the last time, the supernatant should be discarded as completely as possible, and the protein-antibody-Beads complex was resuspended with 50 μl PBS.

0.2 volume of 6× protein loading buffer (300 mmol/L Tris (pH=6.8), 600 mmol/l DTT, 12% SDS, 0.6% bromophenol blue, 60% glycerol) was added to protein sample to be tested. The mixture was boiled for 5 min at 100° C., centrifuged for 10 min at 12000 rpm, and the supernatant was stored at −80° C. before analysis. 10% SDS-PAGE gel was prepared and the protein sample was separated by electrophoresis with constant voltage of 100 v. After electrophoresis, the gel was taken off, and immersed in transfer buffer (39 mmol/l glycine, 48 mmol/l Tris base, 0.037% SDS, 20% methanol) for 10 min. Nitrocellulose membrane (NC membrane) with area slightly larger than the gel (1 cm longer and wider, respectively) was immersed in the transfer buffer for 10 min. A sandwich was prepared by clamping the film and the gel within three layers of filter paper at top and bottom thereof respectively, and placed in electrophoretic transfer tank after pressed and fixed. Transmembrane was carried out with 300 mA constant current for 2.5 h. The membrane was stained with Ponceaux (Ponceau S 2 g; trichloroacetic acid 30 g; sulfosalicylic acid 30 g; diluted to 100 ml) to evaluate whether transmembrane is ok by assessing protein bands. If it is ok, the NC membrane was washed with deionized water for several times, blocked with 5% skim milk for 1 h, and the membrane was washed with TBST for 10 min×3 times, incubated with primary antibody overnight. The next day, the primary antibody was discarded, and the membrane was washed with TBST for 10 min×3 times, and incubated with horseradish peroxidase-labeled goat anti-rabbit secondary antibody for 2 h. The membrane was washed with TBST for 10 min×3 times, and after the last washing, the ECL luminescence liquid reagent (Super Signal West Pico Trial Kit, Pierce) A and B each 1 mL were promptly mixed and reacted on the membrane for about 5 min, placed in fresh-keeping film to be fixed within the X-ray photography dark tray, covered with photographic film rapidly in the dark chamber. The film box was closed and moderately exposed. The film was removed and immediately immersed in the developer solution for 1-2 min, then placed in the fixing solution until the negative film was completely fixed. The film was rinsed and dried, scanned by gel imaging system (Bio-RAD). The images were scanned before data analysis using Quantity One (Bio-RAD) software.

Example 86

ZL006-05 Blocked Glutamate-Induced Coupling of nNOS and PSD-95

Primary neurons were cultured for 10 days in vitro, then the medium was replaced by Locke's medium containing no $Mg^{2+}$ (154 mM NaCl, 5.6 mM KCl, 3.6 mM $NaHCO_3$, 1.3 mM $CaCl_2$, 5.6 mM d-glucose and 5 mM HEPES, pH 7.4). 50 μM glutamate and 30 μM glycine were added and incubated for 30 minutes to induce excitotoxicity, then co-immunoprecipitation was carried out according to the method of Example 17. As shown in FIG. 1, 10 μM ZL006-05 significantly inhibited glutamate-induced coupling of nNOS and PSD-95.

Analgesic Effects of the Objective Compounds on Neuropathic Pain and Inflammatory Pain Example 87

Preparation Method for Neuropathic Pain Model

Neuropathic pain model was prepared by segmental spinal nerve ligation (SNL). The mice were anesthetized by intraperitoneal injection of 2% chloral hydrate (0.2 mL/10 g), after the loss of righting reflex, the mice were fixed in the prone position. The model was prepared by the method of Kim and Chung: a median skin incision with about 3-5 cm length in L4-S2 level of the mouse back was bluntly dissected, the muscles next to the vertebrae till the sixth lumbar protruding were separated, the L5/L6 joint protruding on the right side was exposed and excised, and L6 processes transverses was partially splitted so that the L4-L6 spinal nerves on the right side were exposed. L5 nerve was gently isolated and tightly ligated with 5-0 silk thread. Then the incision was sutured layer by layer, the skin was disinfected with povidone iodine, and the mice were continued to be raised. Postoperative gait deformity appeared in the animals, and in addition to mild valgus and toes were held together in surgery side hind limb, there was no other abnormal change.

Example 88

Preparation Method for Inflammatory Pain Model

Meller method was employed. Skin around the left planta was disinfect with 75% ethanol, and 10 μl Complete Freund's adjuvant (CFA) was injected subcutaneously in planta of right hind limb. The planta was gently pressed with a dry cotton ball after the injection to avoid liquid spill along the pinhole. Mice would usually return to normal within a few minutes. CFA-induced inflammatory pain is a widely used chronic pain model. Animals with CFA inflammation exhibited foot swelling, thermal and mechanical hyperalgesia.

Example 89

Determination Method for Mechanical Pain Threshold

When measuring paw withdrawal threshold (PWT) response to mechanical stimulus, von Frey filaments were used to calculate the threshold for 50% paw withdrawal. Determination of the threshold for 50% paw withdrawal refers to mechanical strength that can cause 50% paw withdrawal response by repeated mechanical stimulus, and touch stimuli (Touch-Test™ sensory evaluator test, produced by U.S. North coast medical, Inc.) was used in this experiment to determine the threshold for 50% paw withdrawal of mice's hind toes by a method of up-and-down. The hind limbs were stimulated by forces of 0.02, 0.04, 0.07, 0.16, 0.4, 0.6, 1.0, 1.4 and 2.0 g. A plexiglas box (45 cm×5 cm×11 cm) was placed on a metal sieve. After the mice were adapted to the plexiglass box for 30 minutes, mouse's hind media planta was stimulated vertically with the von Frey filaments with a duration ≤4 s. The animal behaviors of lifting the head or licking paws were regarded as positive responses, and vice versa as negative responses. The stimulus was started with a force of 0.4 g, and if no paw withdrawal responses appeared, a stronger force of 0.6 g was selected to stimulate the hind paw; if paw withdrawal responses appeared, a weaker force of 0.16 g was selected to stimulate the hind paw, and so on. When a response was different from that of the previous response (from the presence of paw withdraw responses to the absence of paw withdraw responses or from the absence of paw withdraw responses to the presence of paw withdraw responses), continuously stimulate for four times in sequence (a total of six times) so that the measurement of the threshold for 50% paw withdrawal was completed. If the required force was higher than 2.0 g or less than 0.02 g, the threshold value of that side was directly recorded as 2.0 g or 0.02 g with 30 s interval of each stimulus. In the experiment, consistent measurement techniques should be kept, such as the force direction, speed of applied force and curvature of the filaments, maintenance of stability of the force, force withdrawing speed, etc. Furthermore, the criteria of mice response should be consistent. The threshold for 50% paw withdrawal is calculated using the formula: threshold for 50% paw withdrawal=$10^{log(X)+\kappa\delta}$ (X is the force used in the last stimulus; κ is a coefficient of different stimulation modes, which can be looked up in the coefficient table; δ refers to average adjacent distance of the stimulation forces and herein δ=0.224).

Example 90

Determination Method for Thermal Pain Threshold

When measuring paw withdrawal threshold (PWT) responding to thermal stimulus, the latency of paw withdrawal response was determined using pain measurement system of plantar thermal stimulus (UGO BASILE, Italy) which was commercially available. The mice were placed in a small plastic chamber located above a glass platform. The temperature of glass platform was controlled at 22° C. Animals' planta were stimulated with infrared radiator. To prevent tissue damage, the stimulated duration was limited within 30 seconds. If the stimulation time overran, the infrared radiator was automatically turned off. The pain threshold is represented by the time from starting stimulation to the foot removing from the glass platform. To ensure the consistency of the experiment, the sites of the animals receiving the thermal stimulus all located in the center of the hind planta.

Example 91

Composition Forms and Administration Modes of the Drug in Pharmacodynamic Test

When the drug was administered by gavage, the objective compounds milled into a fine powder were suspended with water and sodium carboxymethyl cellulose, wherein the amount of sodium carboxymethyl cellulose was 1%. After the suspension, the objective compounds should be suspended homogeneously in the liquid, and no granular objects would settle or flocculently suspend in the liquid. When the drug was administered by injection, the objective compounds milled into a fine powder were dissolved with 4% Tween 80 after diluted with saline to the desired concentration.

Example 92

Analgesic Effect of Gavage with ZL006-05 on Neuropathic Pain—Dose-Effect/Time-Effect Relationships (Mechanical Pain)

Figure 2:
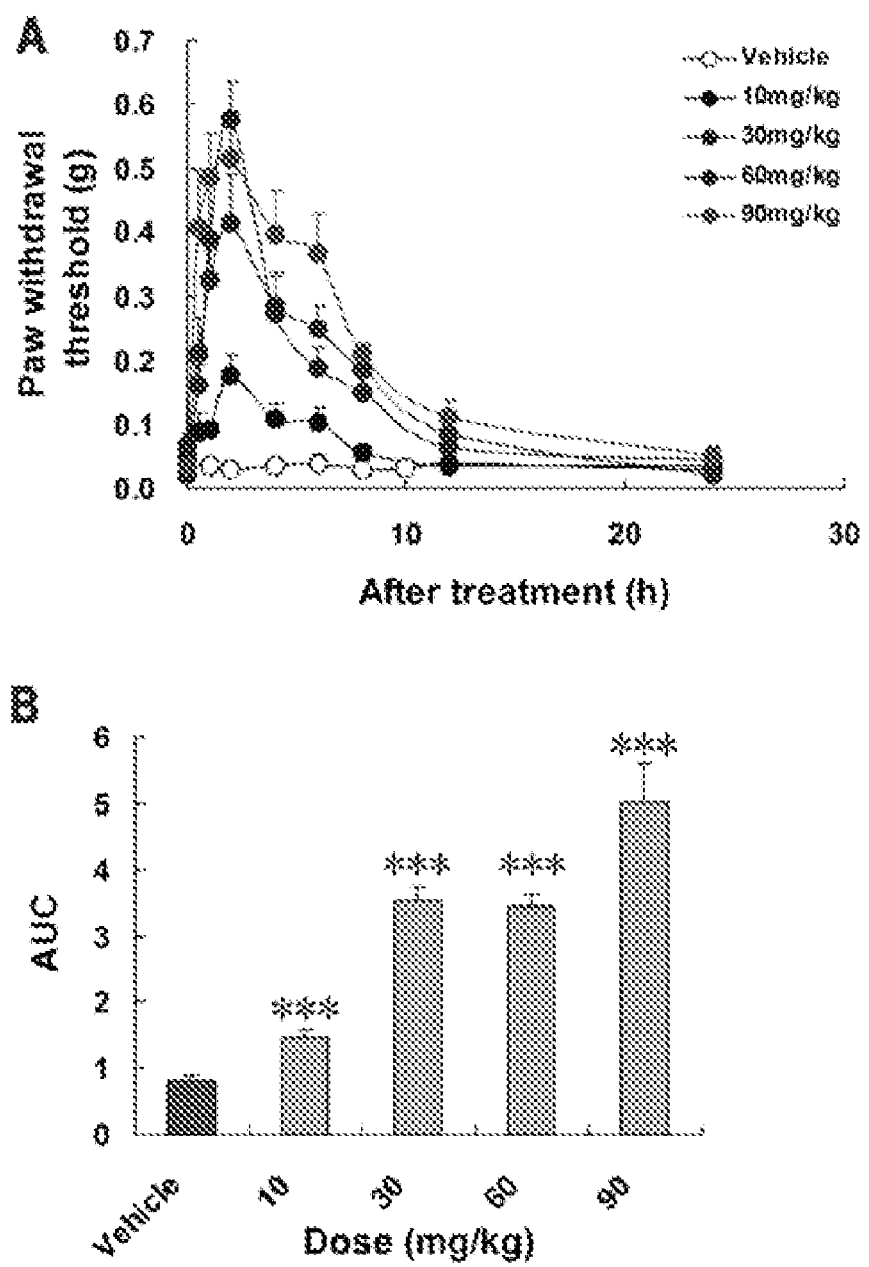
FIG. 2: Analgesic effect of ZL006-05 (intragastrical administration) on neuropathic pain in mice (mechanical stimulus). (2A) Dose-effect and time-effect relationship curves. (2B) Area under the time-effect relationship curve. The threshold baseline of paw withdrawal response to mechanical stimulus was measured prior to SNL surgery. Mean±standard error, n=9~10, ***P<0.001, compared with the vehicle group.

SNL surgery was conducted on the mice whose baseline of threshold for 50% paw withdrawal response to mechanical stimulus was determined. On day 7 after the surgery, the mice were randomly divided into ZL006-05 dose group and vehicle group, respectively dosed by gavage with same volume but different doses of ZL006-05 or equivalent volume of 1% suspension of sodium carboxymethyl cellulose, wherein the doses of ZL006-05 were 10, 30, 60 and 90 mg/kg, respectively. Changes of threshold of paw withdrawal response to mechanical stimulus were measured one hour before administration (−1 h), and 0.5, 1, 2, 4, 6, 8, 10, 12, 24 hours after administration. The results are shown in FIG. 2A, ZL006-05 significantly increased the threshold of paw withdrawal response to mechanical stimulus in a dose dependent manner, wherein 10 mg/kg showed significant efficacy, and the time to show efficacy was less than 0.5 h after administration, a peak time of efficacy appeared at 2 h after administration, and a single dose would make an efficacy duration of about 8 hours. At peak time points of efficacy, pain thresholds of 60 and 90 mg/kg group were about 20 times as the control group. Area under the curve (AUC) was calculated with dose-time curves of 12 h after administration of each dose group, and the drug showed a good dose-response relationship. Compared with the vehicle group, AUC of 90 mg/kg group was about six times as the control group (FIG. 2B).

Example 93

Analgesic Effect of Gavage with ZL006-05 on Neuropathic Pain—Dose-Effect/Time-Effect Relationships (Thermal Pain)

Figure 3:
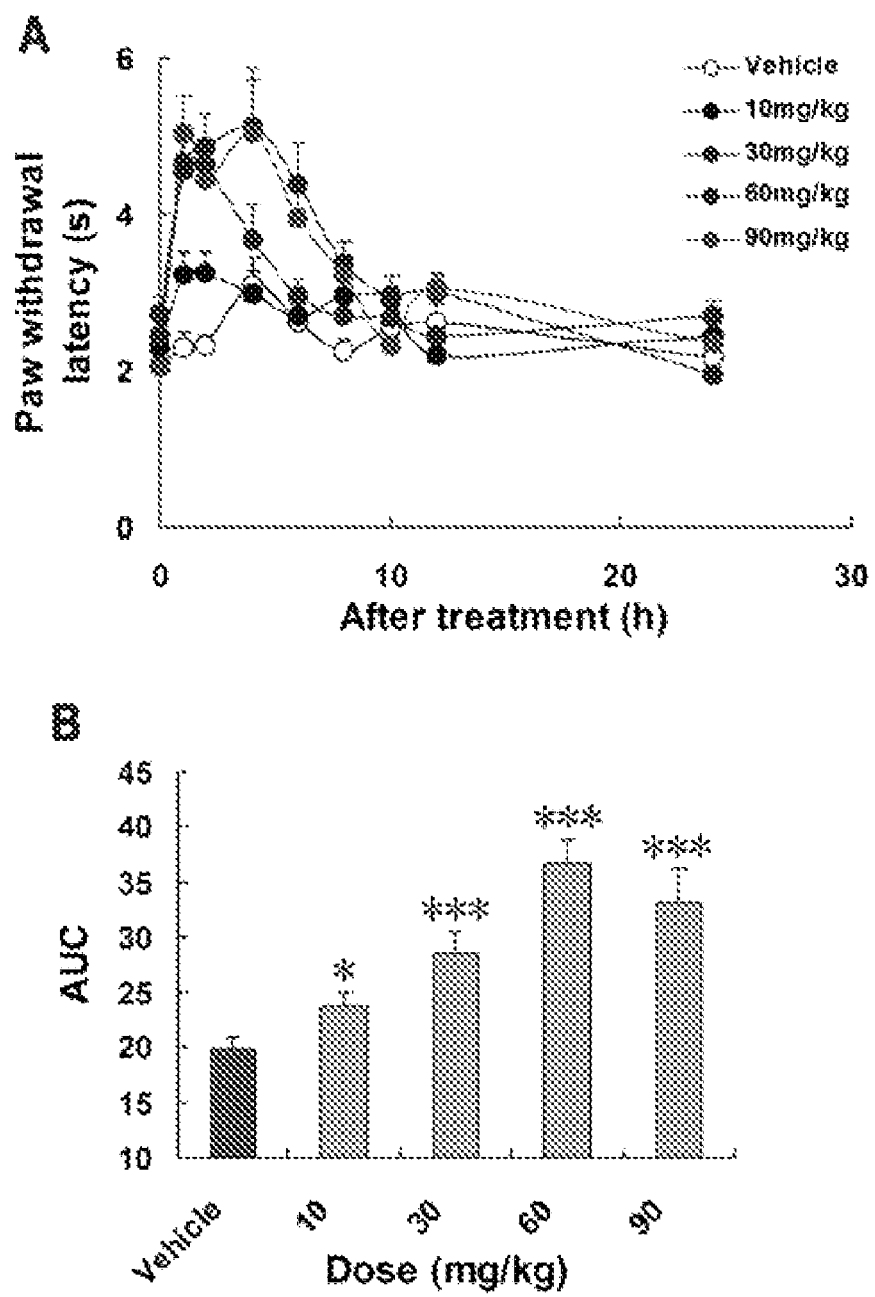
FIG. 3: Analgesic effect of ZL006-05 (intragastrical administration) on neuropathic pain in mice (thermal radiation stimulus). (3A) Dose-effect and time-effect relationships. (3B) Area under the time-effect relationship curve. The latency of paw withdrawal response to thermal radiation stimulus was measured prior to SNL surgery. Mean±standard error, n=10~11, *P<0.05, ***P<0.001, compared with the vehicle group.

SNL surgery was conducted on the mice whose baseline of threshold for 50% paw withdrawal response to mechanical stimulus was determined. On day 7 after the surgery, the mice were randomly divided into ZL006-05 dose group and vehicle group, respectively, administered by gavage with same volume but different doses of ZL006-05 or equivalent volume of 1% suspension of sodium carboxymethyl cellulose, wherein the doses of ZL006-05 were 10, 30, 60 and 90 mg/kg, respectively. Latencies of thermal pain responses were measured 0.5, 1, 2, 4, 6, 8, 10, 12 and 24 hours after administration. The results are shown in FIG. 3A, ZL006-05 significantly increased the latency of paw withdrawal response to thermal pain in a dose dependent manner, wherein 10 mg/kg showed significant efficacy, and the time to show efficacy was less than 0.5 h after administration, a peak time of efficacy varied from 1 to 4 h according to different doses, and a single dose would make an efficacy duration of about 8 hours. At peak time points of efficacy, latencies of 60 and 90 mg/kg group were about 2.5 times as the control group. Area under the curve (AUC) was calculated with dose-time curves of 10 h after administration of each dose group, and the drug showed a good dose-response relationship. Compared with the vehicle group, AUC of 60 mg/kg group was about two times as the control group (FIG. 3B).

Example 94

Analgesic Effect of Gavage with ZL006-05 on Inflammatory Pain—Time-Effect Relationship (Mechanical Pain)

Figure 4:
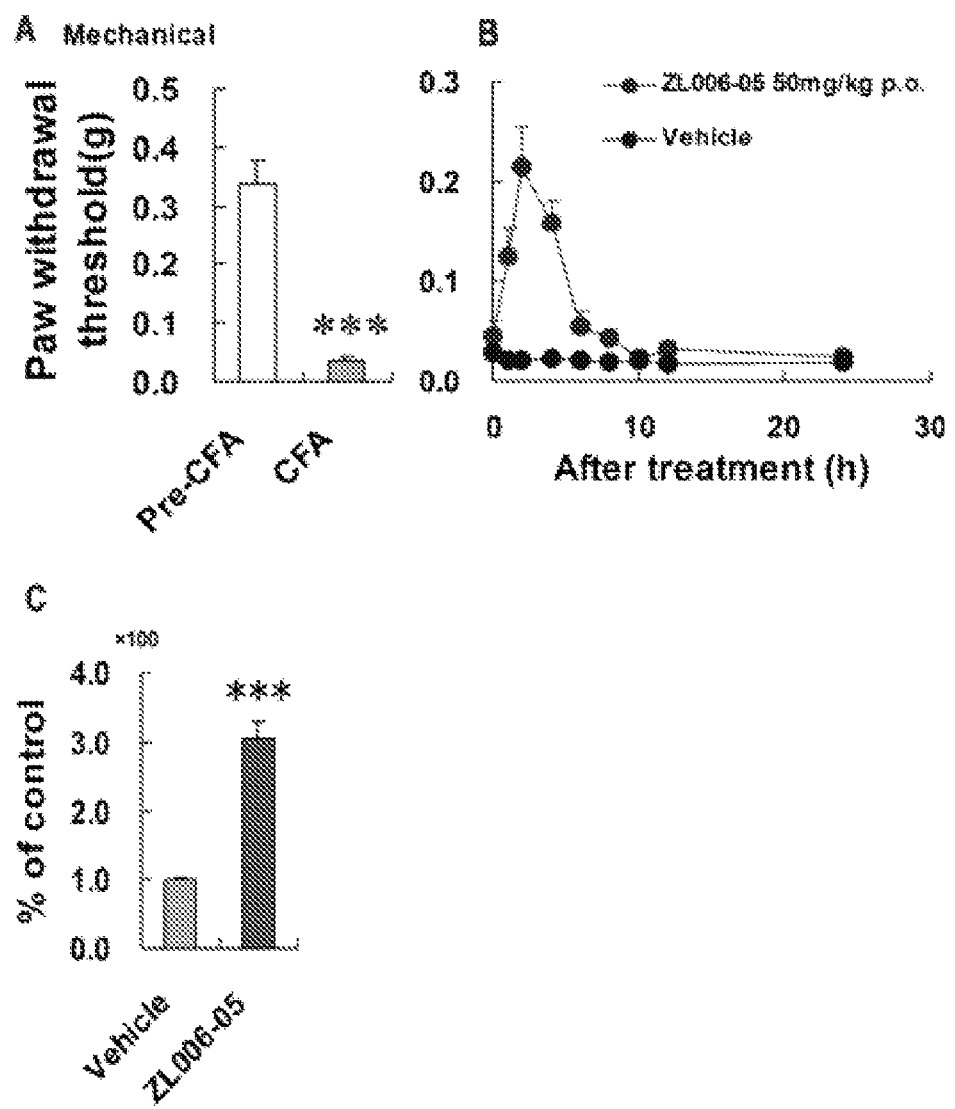
FIG. 4: Analgesic effect of ZL006-05 (intragastrical administration) on inflammatory pain in mice (mechanical stimulus). (4A) The effect of CFA on the threshold of paw withdrawal response to mechanical stimulus. (4B) Changes of threshold of paw withdrawal response to mechanical stimulus at different times after treatment with 50 mg/kg ZL006~05. The threshold baseline of paw withdrawal response to mechanical stimulus was measured prior to SNL surgery. (4C) Area under the time-effect curve of the two groups of animals, normalized to the percentage of solvent control. Mean±standard error, n=9~10, ***P<0.001, compared with the vehicle group.

CFA was injected in the planta of the mice whose baseline of threshold for 50% paw withdrawal response to mechanical stimulus was determined to induce inflammatory pain. The inflammation modeling mice were randomly divided into ZL006-05 dose group and vehicle group, respectively, administered by gavage with ZL006-05 or equivalent volume of 1% suspension of sodium carboxymethyl cellulose, wherein the dose of ZL006-05 was 50 mg/kg. Changes of threshold of paw withdrawal response to mechanical stimulus were measured 0.5, 1, 2, 4, 6, 8, 10, 12 and 24 hours after administration. The results are shown in FIG. 4A, CFA-induced inflammation significantly reduced the threshold of paw withdrawal response to mechanical stimulus, while ZL006-05 significantly increased the threshold of paw withdrawal response to mechanical stimulus, showing significant efficacy 1 h after administration, and a single dose would make an efficacy duration of about 6 hours (FIG. 4B). Within 10 h after administration, areas under the curve of threshold of paw withdrawal response to mechanical stimulus showed significant differences between groups. The area of the dose group was approximately 4 times as that of the control group (FIG. 4C), indicating ZL006-05 has a strong analgesic effect on mechanical hyperalgesia induced by inflammation.

Example 95

Analgesic Effect of Gavage with ZL006-05 on Inflammatory Pain—Time-Effect Relationship (Thermal Pain)

Figure 5:
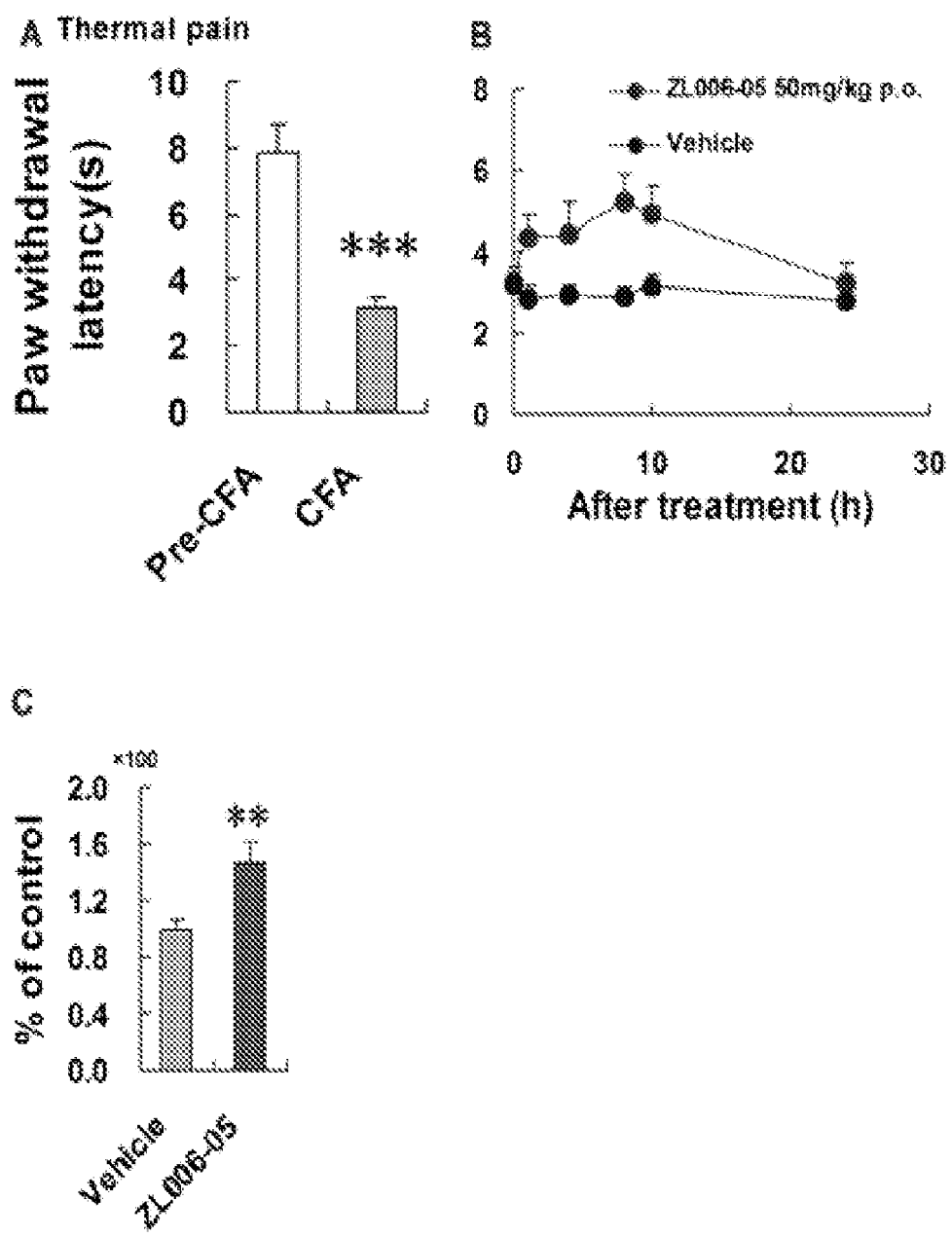
FIG. 5: Analgesic effect of ZL006-05 (intragastrical administration) on inflammatory pain in mice (thermal radiation stimulus). (5A) The effect of CFA on the threshold of paw withdrawal response to mechanical stimulus. (5B) Changes of threshold of paw withdrawal response to mechanical stimulus at different times after treatment with 50 mg/kg ZL006-05. (5C) Area under the time-effect curve of the two groups of animals, normalized to the percentage of solvent control. Mean±standard error, n=10~11, P<0.1, *P<0.001, compared with the vehicle group.

CFA was injected in the planta of the mice whose latency baseline of thermal pain paw response was determined to induce inflammatory pain. The inflammation modeling mice were randomly divided into ZL006-05 dose group and vehicle group, respectively, administered by gavage with ZL006-05 or equivalent volume of 1% suspension of sodium carboxymethyl cellulose, wherein the dose of ZL006-05 was 50 mg/kg. Latencies of paw withdraw response to thermal pain were measured 0.5, 1, 4, 8, 10 and 24 hours after administration. The results are shown in FIG. 5A, CFA induced significant low threshold of paw withdrawal response to thermal stimulus, while ZL006-05 significantly prolonged latencies of paw withdraw response to thermal pain, showing significant efficacy 1 h after administration. A single dose of ZL006-05 maintained an significant analgesic effect about 10 hours (FIG. 5B). Within 10 h after administration, areas under the curve of threshold of paw withdrawal response to mechanical stimulus showed significant differences between groups. The area of the treatment group was approximately 2 times as that of the control group (FIG. 5C), indicating ZL006-05 has a strong analgesic effect on thermal stimulus-induced inflammatory pain.

Example 96

Analgesic Effect of Gavage with ZL006-06, ZL006-16, ZL006-28, ZL006-30, ZL006-43, ZL006-82 on Neuropathic Pain—Time-Effect Relationships (Mechanical Pain)

Figure 6:
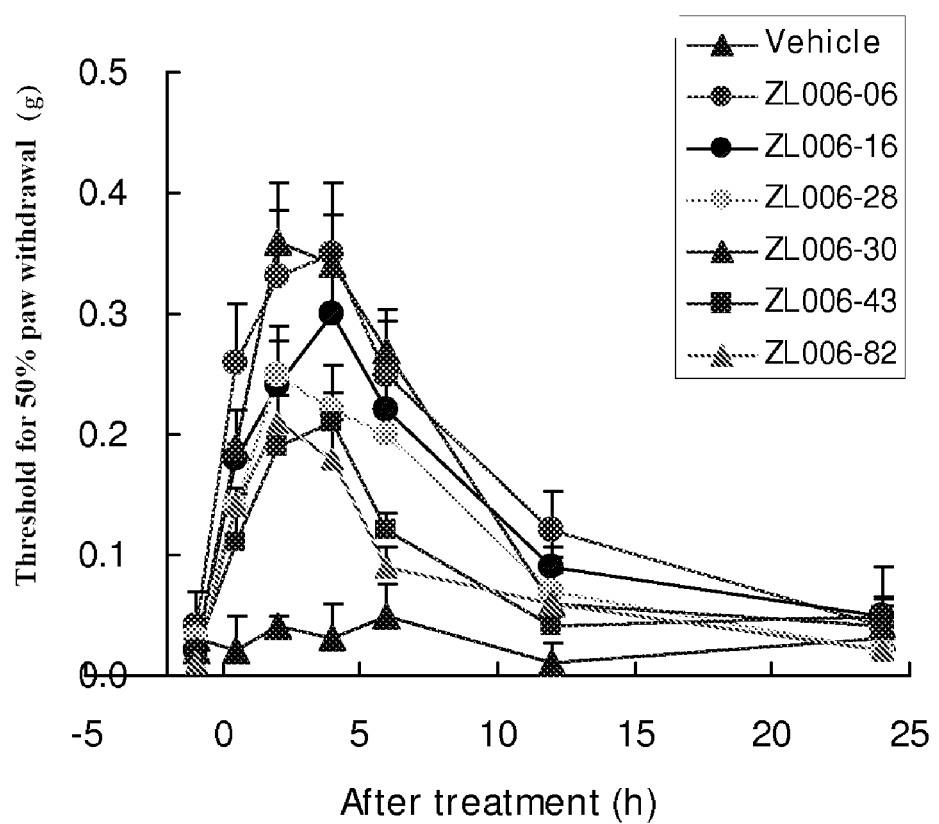
FIG. 6: Analgesic effects of ZL006-06, ZL006-16, ZL006-28, ZL006-30, ZL006-43, ZL006-82 (intragastrical administration) on neuropathic pain in mice (mechanical stimulus). The threshold baseline of paw withdrawal response to mechanical stimulus was measured prior to SNL surgery. Changes of threshold of paw withdrawal response to mechanical stimulus were determined at different times after treatments. Mean±standard error, n=9~10.

SNL surgery was conducted on the mice whose baseline of threshold for 50% paw withdrawal response to mechanical stimulus was determined. On day 7 after the surgery, the mice were randomly divided into ZL006-06, ZL006-16, ZL006-28, ZL006-30, ZL006-43, ZL006-82 dose group and vehicle group, respectively. ZL006-06, ZL006-16, ZL006-28, ZL006-30, ZL006-43, ZL006-82 or equivalent volume of 1% suspension of sodium carboxymethyl cellulose was given by intragastric administration, wherein the doses of each dose group were 40 mg/kg. Changes of threshold of paw withdrawal response to mechanical stimulus were measured one hour before administration (−1 h), and 0.5, 1, 2, 4, 6, 12, 24 hours after administration. The results are shown in FIG. 6, each of ZL006-06, ZL006-16, ZL006-28, ZL006-30, ZL006-43, ZL006-82 significantly increased the threshold of paw withdrawal response to mechanical stimulus, showing significant efficacy 0.5 h after administration, and a single dose would make an efficacy duration of about 6 hours.

Protective Effects of the Objective Compounds on Neuronal Hypoxic Injury and Focal Cerebral Ischemia Reperfusion Injury Example 97

Cell Viability Assay

After primary neurons were cultured for 9 days, the medium was replaced by DMEM high glucose medium containing 1% FBS, serum-starved overnight and then washed twice with OGD culture solution. This OGD culture solution contains DMEM medium, 1% FBS, 1% penicillin/streptomycin and B27, and contains no sugar. Then, the primary neurons were incubated with the test drugs for 30 minutes, OGD culture solution was added into an anaerobic tank and oxygen-deprived for 2 hours. The OGD culture solution was discarded, and replaced by oxygen-saturated DMEM medium containing 1% FBS, 1% penicillin/streptomycin and B27. After 8 hours the culture solution was collected to measure LDH level.

After the primary cortical neurons were treated with various processes, neuronal culture solution in six-well plates was pipetted to a 1.5 mL plastic centrifuge tube; cells were washed three times with PBS solution and each well was added PBS 1000 µl. The cells were freezed and thawed repeated for three times, centrifuged at 12000' g for 5 minutes at 4° C., and the supernatant was removed for use. The activity of LDH enzyme was determined with 50 µl culture solution and 25 µl supernatant using lactate dehydrogenase kit.

Example 98

Preparation of Focal Cerebral Ischemia Reperfusion Model

Cerebral ischemia injury was induced by middle cerebral artery occlusion (MCAO) reperfusion model. After the rats were anesthetized by 2% chloral hydrate (0.2 ml/10 g, i.p.), the animals were fixed supine on the operating table. The neck skin was incised along median line, and neck muscle tissue was bluntly dissected to expose and carefully isolate the common carotid artery (CCA) on the right side. The concomitant vagus nerve was gently peeled and ligated, and inward and superficial external carotid artery (ECA) was cut off; pterygopalatine artery, outward branch artery near skull base along internal carotid artery (ICA), was isolated and ligated. Proximal end of CCA was ligated with surgical wire; distal end of ligature was cut to form a small hole with ophthalmic scissors, though which the commercially available nylon line (No. 4/0) prepared by MCAO model for use in surgical was inserted by about 20 mm until a slight resistance appeared, indicating that the front of the line had reached the anterior cerebral artery. At this point, the blood supply to the middle cerebral arteries (MCA) including carotid artery and ramus communicans before Waldeyer's ring were all blocked. The depth of the inserted line was determined based on the mark. Extravascular part of the line was ligated and fixed to prevent the line from slippage. After rightside cerebral ischemia 120 minutes, the line was carefully unplugged and the broken end was ligated to achieve reperfusion after ischemia. Suturing the skin, and the rats were returned to cage and fed carefully. The body temperature of the animals was maintained constantly at 37±0.5° C. during surgery.

Example 99

Evaluation of Neurological Defect Symptoms of Rats with Focal Cerebral Ischemia Reperfusion Injury The modified Bederson 5-score method was used for evaluation of neurological defect symptoms. Neurological defect symptoms of rats after cerebral ischemia was evaluated by single-blinded method, i.e., test animals were marked by group by the test designers and testers who graded neurological defect symptoms didn't know the animal grouping, after the grading the testers submitted the grading results with various marks to the designers, and the designers unblinded the grouping to obtain scores for each animal in each test group.

| Attached Table: Bederson 5-score method for neurological defect symptoms |
| --- |
| 0: when hanged in the air with tail lifted, the animal stretched two forelimbs to the floor, and no other behavior deficits appeared |
| 1: when hanged in the air with tail lifted, the animal's forelimb (left) opposite to the surgery side performed as wrist elbow flexion, shoulder internal rotation, elbow outward exhibition, clinging to the chest wall |
| 2: the animal was placed on a smooth plate, and when pushing the shoulder of surgery side to the opposite side, the resistance decreased |
| 3: when walking freely, the animal walked along a ring or circled in the direcition opposite to the surgery side |
| 4: flaccid paralysis of limbs occurred, while no spontaneous activity of limbs occurred |

Example 100

Infarct Volume Measurement

The animals were anesthetized with 10% chloral hydrate 3.5 ml/kg, the brains were taken out after beheading, and olfactory bulb, cerebellum and lower brain stem were removed. Blood on the surface of the brain was washed with normal saline and residual water on the surface was absorbed. The brains were placed at −80° C. for 7 min, and once taken out were sliced at the coronal cross planes vertically to the sight plane with 2 mm intervals between the slices. The brain slices were immersed in a water bath (37° C., 90 min) containing 20 g/L TTC dye freshly prepared with 0.2 mol/L pH 7.4~7.8 PBS, and normal brain tissues were stained crimson while ischemic brain tissues were pale. After the tissues were washed with normal saline, the brain slices were rapidly aligned in a row from front to back in order, and the surface residual water was absorbed to dry surface, then photographed. Statistics of the pictures were carried on using image analysis software, and ischemic area (white area) and total area on the right side were delineated. The percentage of cerebral infarct area was calculated using the following formula.

$$\text{infarct area } (\%) = 100 \times \frac{\text{infarct area}}{\text{total area of right hemisphere}}$$

Example 101

Figure 7:
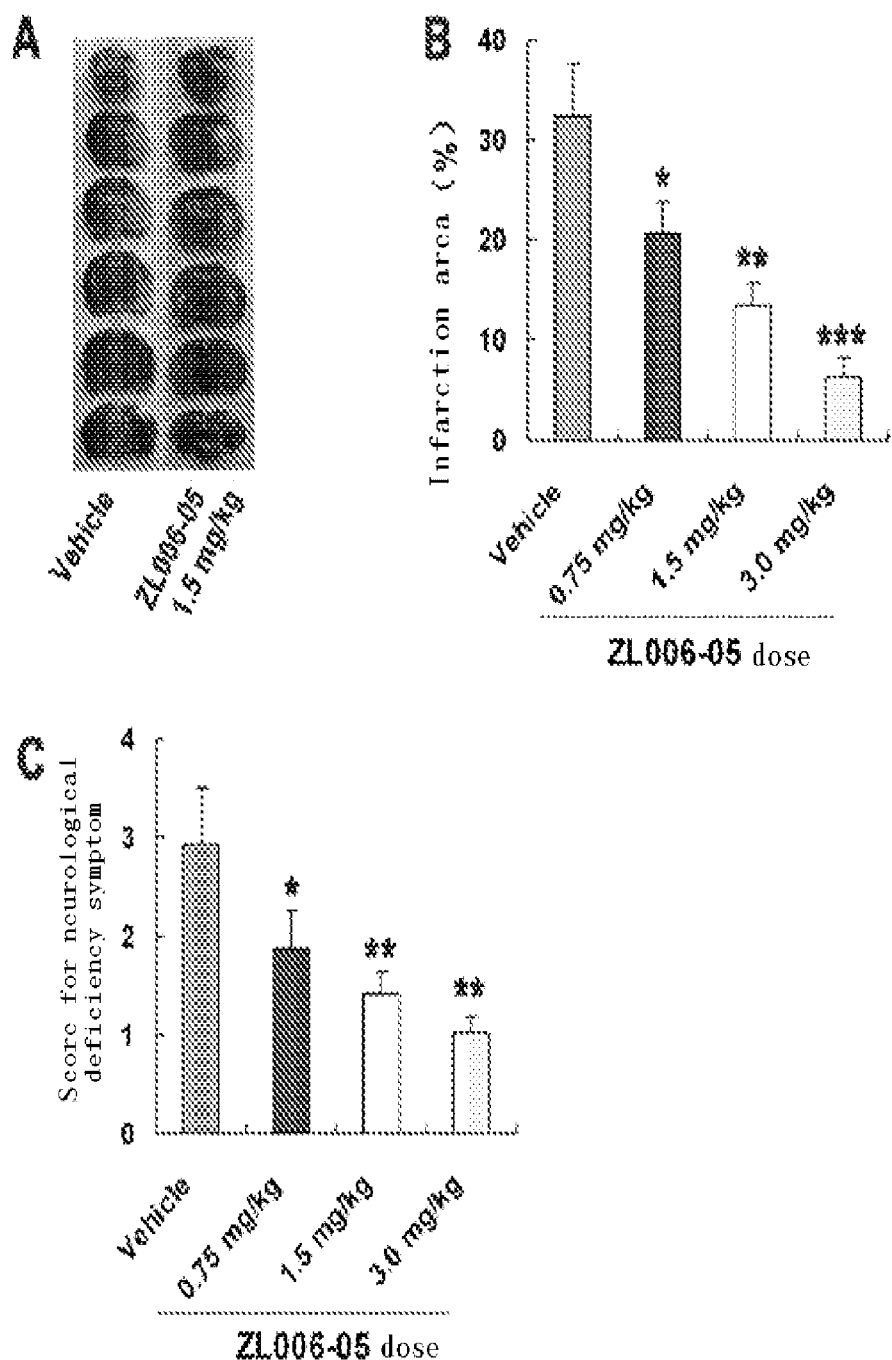
FIG. 7: The dose-effect relationship of protective effect of ZL006-05 (intravenous injection) on acute focal cerebral ischemia/reperfusion injury in rats. MCAO ischemia/reperfusion injury model in rats was employed. The test drugs were injected through tail vein 1 hour after reperfusion, and the cerebral infarct area was determined and neurological deficit symptoms were evaluated 48 hours after reperfusion. (7A) Representative TTC-stained brain sections, showing cerebral infarct area. (7B) Comparison of cerebral infarct areas of each dose group with the vehicle group. (7C) Comparison of neurological defect symptom scores of each dose group with the vehicle group. Mean±standard error, n=10~11, *P<0.05, P<0.1, *P<0.001, compared with the vehicle group.

Protective Effects of ZL006-05 Against Acute Focal Cerebral Ischemia Reperfusion Injury in Rats The rats were under MCAO for 120 min, and 1 h after reperfusion the rats were injected through tail vein with different doses of ZL006-05 or an equivalent volume of solvent, wherein the doses of ZL006-05 were 0.75, 1.5 and 3 mg/kg, respectively, and the volume of injected drugs was 0.1 ml/100 g weight. Neurological deficit symptoms were evaluated 48 h after the cerebral ischemia, then the animals were sacrificed and the brains were taken out, TTC stained, and infarct areas of the stained brain slices were measured. The results were shown in FIG. 7: compared with the control group of solvent, ZL006-05 significantly reduced cerebral infarct area in a dose-dependent manner, and significantly alleviated the neurological defect symptoms.

Example 102

Figure 8:
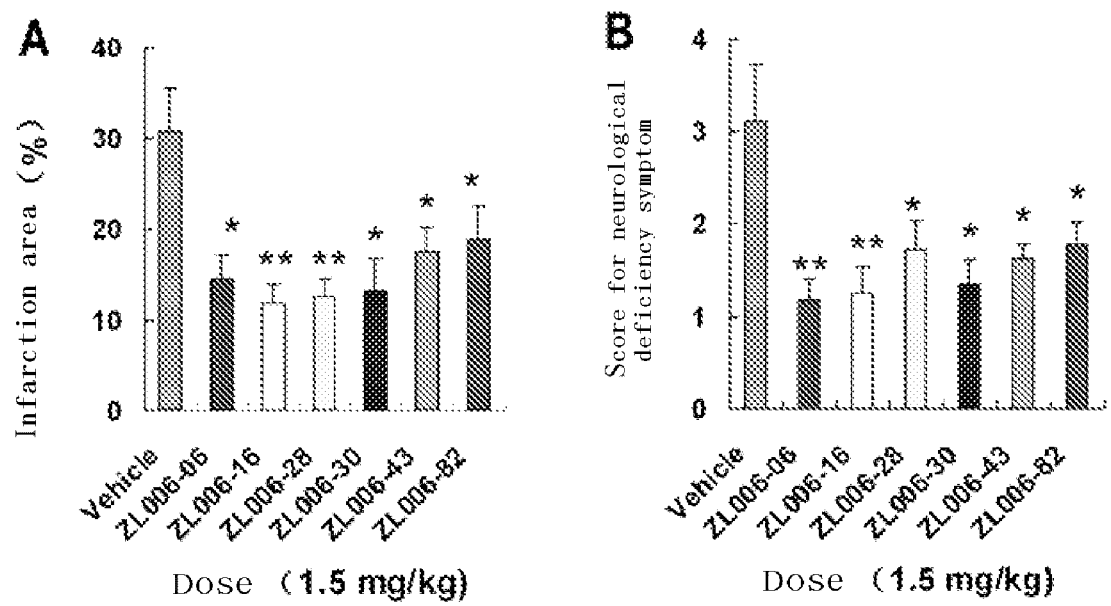
FIG. 8: Protective effects of ZL006-06, ZL006-16, ZL006-28, ZL006-30, ZL006-43, ZL006-82 against acute focal cerebral ischemia/reperfusion injury in rats. MCAO reperfusion injury model in rats was employed. The test drugs were injected through tail vein 1 hour after reperfusion, and the cerebral infarct area was determined and neurological deficit symptoms were evaluated 48 hours after reperfusion. Dose of each drug was 1.5 mg/kg. (8A) Comparison of cerebral infarct areas of each drug with the vehicle group. (8B) Comparison of neurological defect symptom scores of each drug with the vehicle group. Mean±standard error, n=10~11, *P<0.05, **P<0.1, compared with the vehicle group.

Protective Effects of ZL006-06, ZL006-16, ZL006-28, ZL006-30, ZL006-43, ZL006-82 Against Acute Focal Cerebral Ischemia Reperfusion Injury in Rats The rats were under MCAO for 120 min, and 1 h after reperfusion the rats were injected through tail vein with ZL006-06, ZL006-16, ZL006-28, ZL006-30, ZL006-43, ZL006-82 or an equivalent volume of solvent, wherein the doses of each drug were 1.5 mg/kg, and the volume of injected drugs was 0.1 ml/100 g weight. Neurological deficit symptoms were evaluated 48 h after the cerebral ischemia, then the animals were sacrificed and the brains were taken out, TTC stained, and infarct areas of the stained brain slices were measured. The results were shown in FIG. 8: compared with the control group of solvent, each of ZL006-06, ZL006-16, ZL006-28, ZL006-30, ZL006-43 or ZL006-82 significantly reduced cerebral infarct area, and significantly alleviated the neurological defect symptoms.

Example 103

Protective Effects of the Objective Compounds Against Primary Cortical Neuronal Injury Cultured In Vitro (See Table 2)

TABLE 2

Inhibitory effects of the objective compounds on the release of LDH by OGD-injuried neurons

| Comp. No. | Drug concentration (M/L) | Inhibition of LDH release (%) |
|---|---|---|
| ZL006-01 | $10^{-6}$ | 2.3 |
| ZL006-02 | $10^{-6}$ | 21.4 |
| ZL006-03 | $10^{-6}$ | 17.8 |
| ZL006-04 | $10^{-6}$ | 26.9 |
| ZL006-05 | $10^{-6}$ | 62.4 |
| ZL006-06 | $10^{-6}$ | 55.8 |
| ZL006-07 | $10^{-6}$ | 20.7 |
| ZL006-08 | $10^{-6}$ | 50.4 |
| ZL006-09 | $10^{-6}$ | 29.5 |
| ZL006-10 | $10^{-6}$ | 42.3 |
| ZL006-11 | $10^{-6}$ | 41.1 |
| ZL006-12 | $10^{-6}$ | 15.1 |
| ZL006-13 | $10^{-6}$ | 31.4 |
| ZL006-14 | $10^{-6}$ | 19.9 |
| ZL006-15 | $10^{-6}$ | 28.6 |
| ZL006-16 | $10^{-6}$ | 60.3 |
| ZL006-17 | $10^{-6}$ | 48.2 |
| ZL006-18 | $10^{-6}$ | 41.5 |
| ZL006-19 | $10^{-6}$ | 23.9 |
| ZL006-20 | $10^{-6}$ | 11.1 |
| ZL006-21 | $10^{-6}$ | 6.2 |
| ZL006-22 | $10^{-6}$ | 2.5 |
| ZL006-23 | $10^{-6}$ | 18.7 |
| ZL006-24 | $10^{-6}$ | 31.2 |
| ZL006-25 | $10^{-6}$ | 30.6 |
| ZL006-26 | $10^{-6}$ | 35.4 |
| ZL006-27 | $10^{-6}$ | 25.3 |
| ZL006-28 | $10^{-6}$ | 61.6 |
| ZL006-29 | $10^{-6}$ | 41.7 |
| ZL006-30 | $10^{-6}$ | 65.9 |
| ZL006-31 | $10^{-6}$ | 77.3 |
| ZL006-32 | $10^{-6}$ | 36.4 |
| ZL006-33 | $10^{-6}$ | 29.9 |
| ZL006-34 | $10^{-6}$ | 24.1 |
| ZL006-35 | $10^{-6}$ | 12.8 |
| ZL006-36 | $10^{-6}$ | 10.4 |
| ZL006-37 | $10^{-6}$ | 40.2 |
| ZL006-38 | $10^{-6}$ | 41.3 |
| ZL006-39 | $10^{-6}$ | 81.2 |
| ZL006-40 | $10^{-6}$ | 41.8 |
| ZL006-41 | $10^{-6}$ | 45.5 |
| ZL006-42 | $10^{-6}$ | 37.7 |
| ZL006-43 | $10^{-6}$ | 68.9 |
| ZL006-44 | $10^{-6}$ | 43.5 |
| ZL006-45 | $10^{-6}$ | 67.2 |
| ZL006-46 | $10^{-6}$ | 72.5 |
| ZL006-47 | $10^{-6}$ | 84.2 |
| ZL006-48 | $10^{-6}$ | 21.1 |
| ZL006-49 | $10^{-6}$ | 32.6 |
| ZL006-50 | $10^{-6}$ | 40.2 |
| ZL006-51 | $10^{-6}$ | 66.3 |
| ZL006-52 | $10^{-6}$ | 40.5 |
| ZL006-53 | $10^{-6}$ | 61.1 |
| ZL006-54 | $10^{-6}$ | 74.2 |
| ZL006-55 | $10^{-6}$ | 36.3 |
| ZL006-56 | $10^{-6}$ | 50.0 |
| ZL006-57 | $10^{-6}$ | 23.6 |
| ZL006-58 | $10^{-6}$ | 25.1 |
| ZL006-59 | $10^{-6}$ | 61.7 |
| ZL006-60 | $10^{-6}$ | 68.4 |
| ZL006-61 | $10^{-6}$ | 56.5 |
| ZL006-62 | $10^{-6}$ | 50.1 |
| ZL006-63 | $10^{-6}$ | 22.8 |
| ZL006-64 | $10^{-6}$ | 25.4 |
| ZL006-65 | $10^{-6}$ | 38.2 |
| ZL006-66 | $10^{-6}$ | 13.3 |
| ZL006-67 | $10^{-6}$ | 0.4 |
| ZL006-68 | $10^{-6}$ | 1.2 |
| ZL006-69 | $10^{-6}$ | 17.3 |
| ZL006-70 | $10^{-6}$ | 2.4 |
| ZL006-71 | $10^{-6}$ | 7.8 |
| ZL006-72 | $10^{-6}$ | 21.6 |
| ZL006-73 | $10^{-6}$ | 25.3 |
| ZL006-74 | $10^{-6}$ | 24.7 |
| ZL006-75 | $10^{-6}$ | 31.3 |
| ZL006-76 | $10^{-6}$ | 40.5 |
| ZL006-77 | $10^{-6}$ | 44.1 |
| ZL006-78 | $10^{-6}$ | 70.6 |
| ZL006-79 | $10^{-6}$ | 58.3 |
| ZL006-80 | $10^{-6}$ | 41.1 |
| ZL006-81 | $10^{-6}$ | 31.8 |
| ZL006-82 | $10^{-6}$ | 61.2 |
| ZL006-83 | $10^{-6}$ | 33.2 |

The invention claimed is:

1. An N-benzylaniline derivative having the structure of general formula (I),

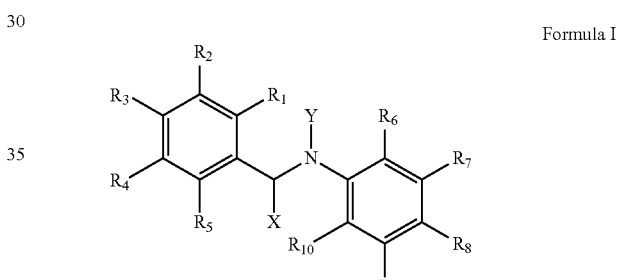

Formula I wherein,
- $R_1$ is hydroxyl, $C_1$-$C_6$ alkoxy or —$OCOR_{11}$;
- $R_2$, $R_3$, $R_5$, $R_6$, $R_9$ or $R_{10}$ is each independently hydrogen, halogen or trifluoromethyl;
- $R_4$ is halogen or trifluoromethyl;
- $R_7$ is —$COR_{12}$, hydroxyl, $C_1$-$C_6$ alkoxy, —$OCH_2COR_{12}$, —$OCOR_{11}$ or —$OCH_2COB$;
- $R_8$ is —$COR_{12}$, hydroxyl, —$OCH_2COR_{12}$, —$OCOR_{11}$ or —$OCH_2COB$;
- X is hydrogen or $C_1$-$C_6$ alkyl;
- Y is hydrogen, $C_1$-$C_6$ alkyl, —$CH_2COR_{13}$ or —$COR_{13}$;
- $R_{11}$ is $C_1$-$C_6$ alkyl or B;
- $R_{12}$ is $C_1$-$C_6$ alkyl, hydroxyl, $C_1$-$C_6$ alkoxy or B;
- $R_{13}$ is $C_1$-$C_6$ alkyl, $C_1$-$C_6$ alkoxy or B;
- B is

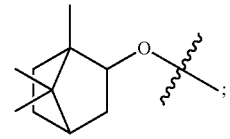 [SMILES: *OC1CC2CCC1(C)C2(C)C]

wherein at least one of $R_7$, $R_8$ and Y contains B group, or a pharmaceutically acceptable salt thereof.

2. The compound as claimed in claim 1, wherein $R_1$ is hydroxyl, $C_1$-$C_4$ alkoxy or $C_1$-$C_4$ alkoxycarbonyl.

3. The compound as claimed in claim 2, wherein $R_1$ is hydroxyl, methoxy or $OCOCH_3$.

4. The compound as claimed in claim 1, wherein $R_2$, $R_3$, $R_5$, $R_6$, $R_9$ or $R_{10}$ is each independently —H, —F, —Cl or —Br; and
$R_4$ is trifluoromethyl, —F, —Cl or —Br.

5. The compound as claimed in claim 1, wherein:
$R_7$ is —COB, —OH, —OCOR$_{11}$, —COR$_{12}$, $C_1$-$C_6$ alkoxy or —OCH$_2$COR$_{12}$;
$R_8$ is —COB, —OH, —OCOR$_{11}$ or —COR$_{12}$;
$R_{11}$ is $C_1$-$C_6$ linear alkoxy; and
$R_{12}$ is hydroxyl, $C_1$-$C_4$ linear alkoxy or B.

6. The compound as claimed in claim 5, wherein:
$R_7$ is —COB, —OH, —OCOCH$_3$, —OCOC$_3$H$_7$, —OCOC$_5$H$_{11}$, —COOCH$_3$, —COOH, —COOC$_2$H$_5$, —OCH$_3$, —OC$_4$H$_9$, —OC$_6$H$_{12}$, —OCH$_2$COOCH$_3$, —OCH$_2$COOC$_2$H$_5$ or —OCH$_2$COB; and
$R_8$ is —COB, —OH, —OCOCH$_3$, —COOCH$_3$, —COOH or —COOC$_2$H$_5$.

7. The compound as claimed in claim 1, wherein:
X is hydrogen or $C_1$-$C_4$ alkyl;
Y is hydrogen, $C_1$-$C_4$ linear alkyl, —CH$_2$COR$_{13}$, —CH$_2$COB or —COR$_{13}$; and
$R_{13}$ is $C_1$-$C_4$ linear alkyl or $C_1$-$C_4$ linear alkoxy.

8. The compound as claimed in claim 7, wherein:
X is hydrogen or methyl; and
Y is hydrogen, —CH$_3$, —COCH$_3$, —CH$_2$COOC$_2$H$_5$, —CH$_2$COB or —CH$_2$COOCH$_3$.

9. The compound as claimed in claim 1, which is selected from the group consisting of:
bornyl-2-hydroxy-5-(2-hydroxy-3,5-dichlorobenzyl) aminobenzoate;
bornyl-2-acetyloxy-5-(2-hydroxy-3,5-dichlorobenzyl) aminobenzoate;
bornyl-2-hydroxy-5-(2-hydroxy-5-chlorobenzyl)aminobenzoate;
bornyl-2-hydroxy-5-(2-hydroxy-5-bromobenzyl)aminobenzoate;
bornyl-2-hydroxy-4-(2-hydroxy-3,5-dichlorobenzyl) aminobenzoate;
bornyl-2-acetyloxy-4-(2-hydroxy-3,5-dichlorobenzyl) aminobenzoate;
bornyl-2-acetyloxy-4-(2-hydroxy-3-chloro-5-fluorobenzyl) aminobenzoate;
bornyl-2-hydroxy-4-(2-hydroxy-3-chloro-5-fluorobenzyl) aminobenzoate;
bornyl-2-hydroxy-4-(2-hydroxy-3,5-dichlorobenzyl) amino-5-chlorobenzoate;
bornyl-2-hydroxy-3-chloro-4-(2-hydroxy-3,5-dichlorobenzyl) aminobenzoate;
bornyl-2-acetyloxy-4-(2-hydroxy-3,5-dichlorobenzyl) amino-5-chlorobenzoate;
bornyl-2-acetyloxy-3-chloro-4-(2-hydroxy-3,5-dichlorobenzyl) aminobenzoate;
bornyl-2-methoxy-4-(2-hydroxy-3,5-dichlorobenzyl) aminobenzoate;
bornyl-2-n-butoxy-4-(2-hydroxy-3,5-dichlorobenzyl) aminobenzoate;
bornyl-2-n-hexyloxy-4-(2-hydroxy-3,5-dichlorobenzyl) aminobenzoate;
bornyl-2-butyryloxy-4-(2-hydroxy-3,5-dichlorobenzyl) aminobenzoate;
bornyl-2-hexanoyloxy-4-(2-hydroxy-3,5-dichlorobenzyl) aminobenzoate;
bornyl-2-methoxy-4-(2-hydroxy-3,5-dichlorobenzyl) amino-5-chlorobenzoate;
bornyl-2-methoxy-3-chloro-4-(2-hydroxy-3,5-dichlorobenzyl) aminobenzoate;
bornyl-2-hydroxy-4-[N-(2-hydroxy-3,5-dichlorobenzyl)-N-methyl] aminobenzoate;
bornyl-2-hydroxy-4-[N-(2-hydroxy-3,5-dichlorobenzyl)-N-acetyl] aminobenzoate;
bornyl-2-methoxy-4-[N-(2-hydroxy-3,5-dichlorobenzyl)-N-methyl] aminobenzoate;
bornyl-2-acetyloxy-4-[N-(2-hydroxy-3,5-dichlorobenzyl)-N-methyl] aminobenzoate;
bornyl-2-acetyloxy-4-[N-(2-hydroxy-3,5-dichlorobenzyl)-N-acetyl] aminobenzoate;
bornyl-2-(2-methoxy-2-carbonylethoxy)-4-(2-hydroxy-3,5-dichlorobenzyl)aminobenzoate;
Methyl-2-(bornyl-2-carbonylethoxy)-4-(2-hydroxy-3,5-dichlorobenzyl) aminobenzoate;
bornyl-2-(2-methoxy-2-carbonylethoxy)-4-[N-(2-hydroxy-3,5-dichlorobenzyl)-N-methyl]aminobenzoate;
Methyl-2-(bornyl-2-carbonylethoxy)-4-[N-(2-hydroxy-3,5-dichlorobenzyl)-N-acetyl]aminobenzoate;
bornyl-2-(2-ethoxy-2-carbonylethoxy)-4-[N-(2-hydroxy-3,5-dichlorobenzyl)-N-(2-ethoxy-2-carbonylethyl)] aminobenzoate;
bornyl-2-(bornyl-2-carbonylethoxy)-4-[N-(2-hydroxy-3,5-dichlorobenzyl)-N-(bornyl-2-carbonylethyl)]aminobenzoate;
Methyl-2-acetyloxy-4-[N-(2-hydroxy-3,5-dichlorobenzyl)-N-(bornyl-2-carbonylethyl)]aminobenzoate;
bornyl-2-hydroxy-4-(2-hydroxy-3-chloro-5-bromobenzyl) aminobenzoate;
bornyl-2-hydroxy-5-(2-hydroxy-3-chloro-5-bromobenzyl) aminobenzoate;
bornyl-2-methoxy-4-(2-hydroxy-3-chloro-5-bromobenzyl) aminobenzoate;
bornyl-2-n-butoxy-4-(2-hydroxy-3-chloro-5-bromobenzyl) aminobenzoate;
bornyl-2-acetyloxy-4-(2-hydroxy-3-chloro-5-bromobenzyl) aminobenzoate;
bornyl-2-butyryloxy-4-(2-hydroxy-3-chloro-5-bromobenzyl) aminobenzoate;
bornyl-2-hydroxy-4-[N-(2-hydroxy-3-chloro-5-bromobenzyl)-N-methyl] aminobenzoate;
bornyl-2-hydroxy-4-[N-(2-hydroxy-3-chloro-5-bromobenzyl)-N-acetyl] aminobenzoate;
bornyl-2-hydroxy-4-(2-hydroxy-3-chloro-5-trifluoromethylbenzyl) aminobenzoate;
bornyl-2-hydroxy-5-(2-hydroxy-3-chloro-5-trifluoromethylbenzyl) aminobenzoate;
bornyl-2-methoxy-4-(2-hydroxy-3-chloro-5-trifluoromethylbenzyl) aminobenzoate;
bornyl-2-n-butoxy-4-(2-hydroxy-3-chloro-5-trifluoromethylbenzyl) aminobenzoate;
bornyl-2-acetyloxy-4-(2-hydroxy-3-chloro-5-trifluoromethylbenzyl) aminobenzoate;
bornyl-2-butyryloxy-4-(2-hydroxy-3-chloro-5-trifluoromethylbenzyl) aminobenzoate;
bornyl-2-hydroxy-4-[N-(2-hydroxy-3-chloro-5-trifluoromethylbenzyl)-N-methyl]aminobenzoate;
bornyl-2-hydroxy-4-[N-(2-hydroxy-3-chloro-5-trifluoromethylbenzyl)-N-acetyl]aminobenzoate;
bornyl-2-hydroxy-4-(2-hydroxy-3-chloro-5-fluorobenzyl) aminobenzoate;
bornyl-2-hydroxy-5-(2-hydroxy-3-chloro-5-fluorobenzyl) aminobenzoate;

bornyl-2-methoxy-4-(2-hydroxy-3-chloro-5-fluorobenzyl) aminobenzoate;
bornyl-2-n-butoxy-4-(2-hydroxy-3-chloro-5-fluorobenzyl) aminobenzoate;
bornyl-2-acetyloxy-4-(2-hydroxy-3-chloro-5-fluorobenzyl) aminobenzoate;
bornyl-2-butyryloxy-4-(2-hydroxy-3-chloro-5-fluorobenzyl) aminobenzoate;
bornyl-2-hydroxy-4-[N-(2-hydroxy-3-chloro-5-fluorobenzyl)-N-methyl] aminobenzoate;
bornyl-2-hydroxy-4-[N-(2-hydroxy-3-chloro-5-fluorobenzyl)-N-acetyl] aminobenzoate;
bornyl-2-hydroxy-4-(2-hydroxy-5-bromobenzyl) aminobenzoate;
bornyl-2-methoxy-4-(2-hydroxy-5-bromobenzyl) aminobenzoate;
bornyl-2-acetyloxy-4-(2-hydroxy-5-bromobenzyl) aminobenzoate;
bornyl-2-hydroxy-4-(2-hydroxy-5-chlorobenzyl) aminobenzoate;
bornyl-2-methoxy-4-(2-hydroxy-5-chlorobenzyl) aminobenzoate;
bornyl-2-acetyloxy-4-(2-hydroxy-5-chlorobenzyl) aminobenzoate;
bornyl-2-hydroxy-4-(2-hydroxy-5-fluorobenzyl) aminobenzoate;
bornyl-2-methoxy-4-(2-hydroxy-5-fluorobenzyl) aminobenzoate;
bornyl-2-acetyloxy-4-(2-hydroxy-5-fluorobenzyl) aminobenzoate;
bornyl-2-hydroxy-4-(2-hydroxy-5-trifluoromethylbenzyl) aminobenzoate;
bornyl-2-methoxy-4-(2-hydroxy-5-trifluoromethylbenzyl) aminobenzoate;
bornyl-2-acetyloxy-4-(2-hydroxy-5-trifluoromethylbenzyl) aminobenzoate;
bornyl-2-hydroxy-4-(2-methoxy-3,5-dichlorobenzyl) aminobenzoate;
bornyl-2-hydroxy-4-(2-acetyloxy-3,5-dichlorobenzyl) aminobenzoate;
bornyl-2-hydroxy-4-(2-methoxy-3-chloro-5-bromobenzyl) aminobenzoate;
bornyl-2-hydroxy-4-(2-acetyloxy-3-chloro-5-bromobenzyl) aminobenzoate;
bornyl-2-hydroxy-4-(2-methoxy-3-chloro-5-trifluoromethylbenzyl) aminobenzoate;
bornyl-2-hydroxy-4-(2-acetyloxy-3-chloro-5-trifluoromethylbenzyl) aminobenzoate.

10. A method of inhibiting the coupling of nNOS and PSD-95 protein, comprising contacting nNOS and PSD-95 protein with the compound of claim 1, or a pharmaceutically acceptable salt thereof, thereby inhibiting said coupling.

11. A method of treating cerebral apoplexy or chronic pathologic pain in an individual in need thereof, comprising administering to said individual the compound of claim 1, or a pharmaceutically acceptable salt thereof.

* * * * *